(12) United States Patent
Becker

(10) Patent No.: US 10,111,860 B1
(45) Date of Patent: Oct. 30, 2018

(54) COMPOSITIONS AND METHODS FOR TREATING CONCUSSION

(71) Applicant: ARISTEA TRANSLATIONAL MEDICINE CORPORATION, Park City, UT (US)

(72) Inventor: Robert E. Becker, Park City, UT (US)

( * ) Notice: Subject to any disclaimer, the term of this patent is extended or adjusted under 35 U.S.C. 154(b) by 0 days.

(21) Appl. No.: 15/590,213

(22) Filed: May 9, 2017

Related U.S. Application Data

(63) Continuation-in-part of application No. 15/406,187, filed on Jan. 13, 2017, now abandoned.

(60) Provisional application No. 62/279,457, filed on Jan. 15, 2016.

(51) Int. Cl.
| | | |
|---|---|---|
| *A61K 31/407* | (2006.01) | |
| *A61K 31/616* | (2006.01) | |
| *A61K 31/167* | (2006.01) | |
| *A61K 31/573* | (2006.01) | |
| *A61K 45/06* | (2006.01) | |
| *A61K 9/20* | (2006.01) | |
| *A61K 9/48* | (2006.01) | |
| *A61K 9/00* | (2006.01) | |
| *G01N 33/80* | (2006.01) | |

(52) U.S. Cl.
CPC .......... *A61K 31/407* (2013.01); *A61K 9/0053* (2013.01); *A61K 9/20* (2013.01); *A61K 9/48* (2013.01); *A61K 31/167* (2013.01); *A61K 31/573* (2013.01); *A61K 31/616* (2013.01); *A61K 45/06* (2013.01); *G01N 33/80* (2013.01); *G01N 2333/918* (2013.01)

(58) Field of Classification Search
CPC ...... A61K 31/407; A61K 9/0053; A61K 9/20; A61K 9/48; A61K 31/167; A61K 31/573; A61K 31/616; A61K 45/06
USPC ........................................................ 514/171
See application file for complete search history.

(56) References Cited

U.S. PATENT DOCUMENTS

| | | | |
|---|---|---|---|
| 5,409,948 | A | 4/1995 | Greig et al. |
| 5,998,460 | A | 12/1999 | Brossi et al. |
| 8,691,864 | B2 | 4/2014 | Greig et al. |
| 2005/0182044 | A1 | 8/2005 | Bruinsma |
| 2007/0129350 | A1 | 6/2007 | Bruinsma |
| 2015/0011584 | A1* | 1/2015 | Mouthon ............... A61K 45/06 514/317 |

FOREIGN PATENT DOCUMENTS

| | | |
|---|---|---|
| CA | 2465600 | 4/2004 |
| CA | 2508585 | 5/2005 |
| EP | 1490057 | 10/2003 |
| EP | 1718294 | 8/2005 |
| WO | WO 2005/091987 | 10/2005 |
| WO | WO 2005/092009 | 10/2005 |
| WO | WO 2005/123068 | 12/2005 |

OTHER PUBLICATIONS

Winblad et al., J Alzheimenrs Dis., 2010, 22(4), 1201-1208).*
Shaw et al. Journal of Neurotrauma, 2013, 30, 557-564 (Year: 2013).*
Abner et al., "Plasma neuronal exosomal levels of Alzheimer's disease biomarkers in normal aging", Ann Clin Transl Neurol, 2016, 3(5): p. 399-403.
Agrawal et al., "The modified Romberg Balance Test: normative data in U.S. adults", Otol Neurotol, Oct. 2011, 32(8):1309-1311.
Akiyama et al., "inflammation and alzheimer's disease", neurobiol aging, 2000, 21(3):383-421.
Alexander, "Mild traumatic brain injury: pathophysiology, natural history and clinical management", Neurology, 1995, 45:1253-1260.
Angrist et al., "Identification of Casual Effects using Instrumental Variables", J Am Statist Assoc 1996, 91(434):444-445.
Auble et al., "Hypopituitarism in pediatric survivors of inflicted traumatic brain injury", Feb. 15, 2014, K. of Neurotrauma, 31:321-326.
Bains et al., "antioxidant therapies in traumatic brain and spinal cord injury", biochim biophys acta, May 2012, 1822(5):675-684.
Baratz et al., "transiently lowering tumor necrosis factor-alpha synthesis ameliorates neuronal cell loss and cognitive impairments induced by minimal traumatic brain injury in mice", j neuroinflammation, 2015, 12:45, pp. 1-14.
Barker-Collo et al., "Prevalence, natural course and predictors of depression 1 year following traumatic brain injury from a population-based study in New Zealand", 2015, Brain Injury, 29:7-8, pp. 859-865.
Barker-Collo et al., "Sex Differences in Stroke Incidence, Prevalence, Mortality and Disability-Adjusted Life Years: Results from Global Burden of Disease Study 2013", Neuroepidemiology, 2015, 45:203-214.
Barkhoudarian et al., "the molecular pathophysiology of concussive brain injury", clin sports med, Jan. 2011, 3(1):33-48.
Becker, "Lessons from Darwin: 21st century designs for clinical trials", Curr Alz Res, 2007, 4:458-467.

(Continued)

*Primary Examiner* — Yevgeny Valendrod
(74) *Attorney, Agent, or Firm* — Workman Nydegger

(57) ABSTRACT

Compositions and methods for mitigating a pathology following brain trauma or at least a portion of a cascade of a pathology associated therewith, including compositions and methods for treating concussion or preventing the onset of anecrotic cell death in neurons. Exemplary compositions for treating concussion include an active compound comprising one or more of: phenserine, a phenserine metabolite, a phenserine prodrug, or combinations thereof; and one or more pharmaceutically acceptable excipients. The one or more excipients can be combined with the active compound to form an extended, controlled-release medicament that delivers a therapeutic concentration of the active compound over a period of time. Exemplary methods include administering a therapeutic dose of the active compound and, optionally, a therapeutically acceptable dose of a second active compound, and, optionally, maintaining the therapeutic doses of the active and optional second active compounds at therapeutically effective concentrations over a period of time.

22 Claims, 17 Drawing Sheets

(56) References Cited

OTHER PUBLICATIONS

Becker, "two cultures in modern science and technology: for safety and validity does medicine have to update?", Jan. 11, 2016, J Patient Saf., pp. 1-5.
Becker et al., "A new regulatory road-map for Alzheimer's Disease drug development", Curr. Alz. Res, Mar. 2014, 11(3):215-220.
Becker et al., "A new roadmap for drug development for Alzheimer's disease", Nat Rev Drug Discov, Feb. 2014, 13(2):156, pp.1-5.
Becker et al., "Alzheimer's disease drug development: old problems require new priorities", CNS & neurological disorders-drug targets, Dec. 2008, 7(6):499-511.
Becker et al., "Double-Blind, Placebo-Controlled Study of Metrifonate, an Acetylcholinesterase Inhibitor, for Alzheimer's Disease", Alzheimer's Disease and Associated Disorders, 10(3), 124-131, 1996.
Becker et al., "Effects of Metrifonate on Cognitive Decline in Alzheimer's Disease", Alzheimer's Disease and Associated Disorders, 12(1) 54-57, 1998.
Becker et al., "fire in the ashes: can failed Alzheimer's drugs succeed with second chances?" Alzheimer's and dementia, 2013, 9:50-57.
Becker et al., "lost in translation: Neuropsychiatric drug developments", Sci Transl Med, Dec. 8, 2010, 2(61):1-17.
Becker et al, "Neuropsychiatric clinical trials: should they accommodate to real-world practices or set standards for clinical practices?", J Clin Psychopharm., Feb. 2009, 29(1):56-64.
Becker et al., "Problems arising from the generalizing of treatment efficacy from clinical trials in Alzheimer's disease." Clin Drug Invest, Jan. 2000, 19(1):33-41.
Becker et al., "Resurrecting clinical pharmacology as a contect for Alzheimer disease drug development." curr. Alz. Res., 2009, 6(1):79-81.
Becker et al., "Was phenserine a failure or were investigations mislead by methods?" Curr. Alz. Res, Dec. 2012, 9(10):1174-1181.
Becker et al., "What can triumphs and tribulations from drug research in Alzheimer's disease tell us about the development of psychotropic drugs in general?", the lancet psychiatry, 2015, 2:756-64.
Becker at al., "Why do so many drugs for Alzheimer's Disease fail in development? Time for new methods and new practices?", J Alzheimers Dis, Oct. 2008, 15(2):303-325.
Becker et al., "Why so few drugs for Alzheimer's disease? Are methods failing drugs?",Curr Alz Research, Nov. 1, 2010, 7(7):642-651.
Belhocine et al., "Tc-Annexin A5 quantification of apoptotic tumor response: a systematic review and meta-analysis of clinical imaging trials", Eur J Nucl Med Mol Imaging, 2015, 42(13):2083-2097.
Biondo al., "the interleukin-1beta/CXCL1/2/Neutrophil Axis Mediates Host Protection against Group B Streptococcal infection", infection and immunity, Nov. 2014, 82(11):4508-4517.
Biankenberg et al., In vivo detection and imaging of phosphatidylserine expression during programmed cell death, Proc Natl Acad Sci USA, 95(11):6349-54, 1998.
Blankenberg et al., radionuclide imaging of acute lung transplant rejection with annexin v, Chest., Mar. 2000, 117(3):834-840.
Broadbent et al., "The cognitive failures questionnaire (CFQ) and its correlates", the british journal of clinical psychology, 1982, 21(pt 1):1-16.
Can head trauma cause alzheimer's?, Big Think, accessed on Apr. 19, 2018 via http://bigthink.com/articles/can-head-trauma-cause-alzheimers.
Chan, "what does cognitive failure questionnaire measure? General cognitive failure or specific domain deficits?", archives of clinical neuropsychology, 1999, 14:735-736.
Chen et al., "(-)-Phenserine attenuates soman-induced neuropatholgy", Jun. 2014, PLoS One, 9(6):e99818, pp. 1-12.
Chung et al., "tumor necrosis factor-alpha production by astrocytes, induction by lipopolysaccharide, IFN-gamma, and IL-1 beta", journal of immunology, Apr. 15, 1990, 144(8):2999-3007.
Cohen, "things I have learned (so far)", Amer Psychologist, 45:1304-1312, 1990.
Conidi, "DTI Flags traumatic brain injury in NFL players", medscape, Apr. 13, 2016, paper presented at american academy of neurology (AAN) 2016 Annual Meeting, pp. 1-3.
Crane et al., "association of traumatic brain injury with late-life neurodegenerative conditions and neuropathologic findings", JAMA neurology, Sep. 2016, 73(9):1062-1069.
Daneshvar et al., "long-term consequences: effects on normal development profile after concussion", phys med rahabil clin n am., Nov. 2011, 22(4):683-700.
DeKosky et al., "association of increased cortical soluble abeta42 levels with diffuse plaques after severe brain injury in humans", arch neurol., 64:541-544, 2007.
DeMarshall et al., "detection of alzheimer's disease at mild cognitive impairment and disease progression using autoantibodies as blood-based biomarkers", 2016, Alzheim. & Dement., vol. 3, pp. 51-62.
Dikmen et al., "Neurobehavioural outcomes and their determinants", J. Head Trauma Rehabil., 1995, 10(1):74-86.
Dunn et al., "Estimating treatment effects from randomized clinical trials with noncompliance and loss to follow-up: the role of instrumental variable methods", statis meth med res, 2005, 14:369-395.
Eikelenboom et al., "inflammatory mechanism in alzheimer's disease", trends pharmacol sci, Dec. 1994, 15:447-450.
Eikelenboom et al., "whether, when and how chronic inflammation increase the risk of developing late-onset alzheimer's disease", alzheimer's research & therapy, 4:15, 2012.
Eyres et al., "construct validity and reliability of the rivermead post-concussion symptoms questionnaire", clin rehabil., Dec. 2005, 19(8):878-887.
Fakhran et al., "symptomatic white matter changes in mild traumatic brain injury resemble pathologic features of early alzheimer dementia", radiology, Oct. 2013, 269(1):249-257.
Feddermann-Damont et al., "What domains of clinical function should be assessed after sports-related concussion? A systematic review", 2017, Br J Sports Med, 51:903-918
Fiandaca et al., "Identification of preclinical alzheimer's disease by a profile of pathogenic proteins in neurally derived blood exosomes: a case-control study", alzheimer's dement., 2015, 11:600-607.
Food and Drug Administration, "Good ANDA Submission Practices Guidance for Industry", Jan. 2018, Generics, pp. 1-30, accessed via http://www.fda.gov.downloads.drugs.guidancecomplianceregulatoryinformation/guidances/ucm072974.pdf.
Fratiglioni et al., "Risk factors for late-onset alzheimer's disease: a popuiation-base, case-control study", ann neurol, 1993, 33:258-266.
Gentleman et al., "a beta 42 is the predominant form of amyloid beta-protein in the brains of short-term survivors of head injury", neuroreport, Apr. 14, 1997, 8(6):1519-1522.
Gentleman et al., "long-term intracerebral inflammatory response after traumatic brain injury", forensic sci into., 2004, 146:97-104.
Ghajar, "traumatic brain injury", lancet, Sep. 9, 2000, 356:923-929.
Giza et al., "the neurometabolic cascade of concussion", j athl train, 2001, 36(3):228-235.
Goetzl et al., "altered lysosomal proteins in neural-derived plasma exosomes in preclinical alzheimer disease", neurology, Jul. 7, 2015, 85(1):40-47.
Goetzl et al., "low neural exosomal levels of cellular survival factors in alzheimer's disease", ann clin transl neurol, 2015, 2:769-773.
Goldstein et al., "chronic traumatic encephalopathy in blast-exposed military veterans and a blast neurotrauma mouse model", sci transl med., May 16, 2012, 4(134):134ra69, pp. 1-32.
Gottlieb, "Head injury doubles the risk of alzheimer's disease", BMJ, Nov. 4, 2000, 321:1100.
Greig et al., "amyloid precursor protein synthesis inhibitors for alzheimer's disease treatment", ann neurol. 76:629-630, 2014.
Greig et al., "an overview of phenserine tartrate, a novel acetylcholinesterase inhibitor for the treatment of alzheimers disease", cur. Alz. Res., 2005, 2(3):281-290.
Greif et al., "anticholinesterase and pharmacokinetic profile of phenserine in healthy elderly human subjects" curr alzheimer res., 2005, 2(4):483-492.

(56) References Cited

OTHER PUBLICATIONS

Greig et al., "the experimental alzheimer drug phenserine: preclinical pharmacokinetics and pharmacodynamics", acta reurol scand suppl., 2000, 176-74-84.
Greve et al., "pathophysiology of traumatic brain injury", mt sinai j med., Apr. 2009, 76(2):97-104.
Griffin et al., "the pervasiveness of interleukin-1 in alzheimer pathogenesis: a role for specific polymorphisms in disease risk", exp gerontol, Jul. 2000, 35(4): 481-487.
Gronwall et al., "cumulative effect of concussion", The Lancet, Nov. 22, 1975, 995-997.
Guadagno et al., "Microglia-derived IL-1beta triggers p53-mediated cell cycle arrest and apoptosis in neural precursor cells", cell death and disease, 2015, 6:e1779, pp. 4-10.
Haran et al., "reliable change estimates for assessing recovery from concussion using the ANAM4 TBI-MIL", j head trauma rehabil, Aug. 19, 2015, vol. 31, No. 5, pp. 329-338.
Heneka et al., "Neuroinflammation in Alzheimer's disease", lancet neurol., Apr. 2015, 14(4):338-405.
Hickman et al., "microglial dysfunction and detective beta-amyloid clearance pathways in aging alzheimer's disease mice", j neurosci, Aug. 13, 2008, 28(33):8354-8360.
Hoffer et al., "Neurosensory symptom complexes after acute mild traumatic brain injury", PLoS ONE, Jan. 4, 2016, 11(1):e0146039, pp. 1-12.
Hoge et al., "Mild traumatic brain injury in U.S. soldiers returning from Iraq", n engl j med, Jan. 31, 2008, 358:453-463.
Horsburgh et al., "beta-amyloid (abeta)42(43), abeta42, abeta40 and apoE immunostaining of plaques in fatal head injury", neuropathol appl neurobiol, Apr. 2000, 26(2):124-132.
Hynd et al., "glutamate-mediated excitoxicty and neurodegeneariton in alzheimer's disease", neurochem int., Oct. 2004, 45(5):583-595.
Ikonomovic et al., "alzheimer's pathology in human temporal cortex surgically excised after severe brain injury", exp neurol, 2004, 190:192-203.
Iverson, "Mild traumatic brain injury and risk for alzheimer's disease", IBIA, accessed on Apr. 19, 2018 via http://www.internationalbrain.org/articles/mild-traumatic-brain-injury-risk-for-alzheimers-disease/.
Johnson et al., "axonal pathology in traumatic brain injury", Exp Neurol., Aug. 2013, 246:35-43.
Johnson et al., "inflammation and white matter degeneration persist for years after a single traumatic brain injury", brain, 2013, 136:28-42.
Johnson et al., "widespread tau and amyloid-beta pathology many years after a single traumatic brain injury in humans", Mar. 2012, brain pathol, 22:142-149.
Kapogiannis et al., "Dysfunctionally phosphorylated type 1 insulin receptor substrate in neural-derived blood exomsomes of preclinical Alzheimer's disease", FASEB J, 2015, 29(2):589-596.
Katz et al., "Baseline performance of NCAA athletes on a concussion assessment battery: a report from the CARE consortium", 2018, Sports Medicine, accessed on https://doi.org/10.1007/s40279-018-0875-7.
Kellar et al., "Comparing fMRI activation during smooth pursuit eye movements among contact sport athletes, non-contact sport athletes, and non-athletes", 2018, NeuroImage: Clinical, 18:413-424.
Kemp et al., "The neurological, neuroimaging and neuropsychological effects of playing professional football: results of the UK five-year follow-up study", 2016, Brain Injury, 30:9, pp. 1068-1074.
Kenny, "The Use of Novel PET Tracers to Image Breast Cancer Biologic Processes Such as Proliferation, DNA Damage and Repair, and Angiogenesis", J Nucl Med., Feb. 2016, 57(2) Supplemental 1:89S-95S.
Kiraly and Kiraly, "Traumatic Brain Injury and Delayed Sequelae: A Review—Traumatic Brain Injury and Mild Traumatic Brain Injury (Concussion) are precursors to Later-Onset Brain Disorders, Including Early-Onset Dementia", Sci. World Jor., 2007, 7:1768-1776.
Klein, "Phenserine", Expert Opin Investig Drugs, 2007, 16:1087-1097.
Kondo et al., "cis p-tau: early driver of brain injury and tauopathy blocked by anibody", nature, Jul. 23, 2015, 523(7561):431-436.
Kwak et al., "secreted type of amyloid precursor protein induces glial differentiation by stimulating the BMP/Smad signaling pathway,", biochem biophys res commun., 2014, 447(3):394-399.
Lahiri et al., "The experimental alzheimer's disease drug posiphen lowers amyloid-beta peptide levels in cell culture and mice", J. Pharmacol, Esp. Ther., 2007, 320(1):386-396.
Langlois et al., "the epidemiology and impact of traumatic brain injury: a brief overview", j head trauma rehabil, 2006, 21(5):375-378.
Launer et al., "rates and risk factors for dementia aand alzheimers disease", neurology, Jan. 1999, 52:78-84.
Li et al., "A case control study of alzheimer's disease in China", neurology, Aug. 1992, 42:1481-1488.
Li et al., "Head Injury as a risk factor for dementia and alzheimer's disease: a systematic review and meta-analysis of 32 observational studies", plos one, Jan. 9, 2017, pp. 1-17.
Lilja et al., "age-dependent neuroplasticity mechanisms in alzheimer Tg2576 mice following modulation of brain amyloid-beta levels", PLoS One, Mar. 2013, 8(3):e58752, pp. 1-11.
Lilja et al., "Neurotrophic and neuroprotective actions of (−)- and (+)- phenserine, candidate drugs for alzheimer's disease", PLos One, Jan. 2013, 8(1):e54887, pp. 1-10.
Loane et al., "amyloid precursor protein secretases as therapeutic targets for traumatic brain injury", nat med, Apr. 2009, 15(4):377-379.
Loane et al., "progressive neurodegeneration after experimental brain trauma: association with chronic microglial activation", j neuropathol exp neurol, Jan. 2014, 73(1):14-29.
Marchetti et al., "Temporal and spatial characteristics of gait during performance of the dynamic gait index in people with and people without balance or vestibular disorders", Phys Ther, May 2008, 88(5):640-651.
Marsh et al., "relationship between cognitive deficits and social skill after head injury", neuropsychology, 1991, 5(2):107-117.
Marutle et al., "modulation of human neural stem cell differentiation in Alzheimer (app23) transgenic mice by phenserine", PNAS, Jul. 24, 2007, 104(30):12506-12511.
McAllister et al., "Cognitive effects of head impacts in a cohort of collegiate contact sport athletes", May 29, 2012, Neurology, 78, pp. 1777-1784.
McGeer et al., "targeting microglia for the treatment of alzheimer's disease", expert opin ther targets, 2015, 19(4):497-506.
McKee et al., "the neuropathology of sport", acta neuropathol (berl), 2014, 127:29-51.
McKee et al., "the neuropathology of traumatic brain injury", Handb Clin Neurol, 2015, 127:45-66.
McLean et al., "the behavioral sequelae of head injury", J. Clin. Neuropsychol., 1983, 5:4, 361-376.
McNamara, "Serial mini-concussions: does the brain compensate?", Apr. 23, 2018, Medscape Medical News—Neurology News, pp. 1-3.
Mehta et al., "head trauma and risk of dementia and alzheimer's disease: the rotterdam study", neurology, Dec. 10, 1999, 53(9):1959-1962.
Mielke et al., "head trauma and in vivo measures of amyloid and neurodegeneration in a population-based study", neurology, 82(1):70-6, 2014.
Mild traumatic brain injury committee, "definition of mild traumatic brain injury", J. Head trauma Rehabil, 1993, 8(3):86-87.
Morganti-kossmann et al., "inflammatory response in acute traumatic brain injury: a double-edged sword", curr opin crit care, 2002, 8(2):101-5.
Morganti-Kossmann et al., "modulation of immune response by head injury" injury Int. J., 2007, 38:1392-1400.
Mosca et al., "A patient-side technique for real-time measurement of acetylcholinesterase activity during monitoring of eptastigmine treatment", Ther Drug Monit, 1995, 17:230-238.
Mosher et al., microglial dysfunction in brain aging and alzheimer's disease biochemical pharmacology 88, 2014, 594-604.

(56) References Cited

OTHER PUBLICATIONS

Nakamura et al., "proline isomer-specific antibodies reveal the early pathogenic tau conformation in alzheimer's disease", Mar. 30, 2012, cell., 149(1):232-244.
Oni et al., "diffusion tensor imaging analysis of frontal lobes in pediatric traumatic brain injury", j. child neurol., Aug. 2010, 25(8):976-984.
Petraglia et al., "The pathophysiology underlying repetitive mild traumatic brain injury in a novel mouse model of chronic traumatic encephalopathy", surg neurol int., 2014, 5:184, pp. 1-23.
Plesnila et al., "delayed neuronal death after brain trauma involves p53-dependent inhibition of NF-kappaB transcriptional activity", cell death differ., 14(8):1529-41, 2007.
Povlishock, "traumatically induced axonal injury: pathogenesis and pathobiological implications", brain pathol., Jan. 1992, 2(1):1-12.
Povlishock et al., Axonal change in minor head injury, J Neuropathol Exp Neurol, May 1983, 42(3):225-242.
Rachmany et al., "Cognitive Impairments Accompanying Rodent Mild Traumatic Brain Injury Involve p53-Dependent Neuronal Cell Death and Are Ameliorated by the Tetrahydrobenzothiazole PFT-alpha", PLoS One, Nov. 2013, 8(11):e79837, pp. 1-12.
Raskin et al., "neurobiology of alzheimer's disease: integrated molecular, physiological, anatomical, biomarker, and cognitive dimensions", curr alzheimer res., 2015, 12(8):712-722.
Ray et al., "Molecular and immunocytochemical characterization of primary neuronal cultures from adult rat brain: differential expression of neuronals and glial protein markers", J Neurosci Methods, Nov. 15, 2009, 184(2):294-302.
Reale et al., "Selective Acetyl- and Butyrylcholinesterase Inhibitors Reduce Amyloid-beta Ex Vivo Activation of Peripheral Chemocytokines from Alzheimer's Disease Subjects: exploring the cholinergic anti-inflammatory pathway" Curr Alzheimer Res., 11(6):608-22, 2014.
Roberts et al., "beta A4 amyloid protein deposition in brain after head trauma", lancet, Dec. 7, 1991, 338:1422-1423.
Roberts et al., "beta amyloid protein deposition in the brain after severe head injury: implications for the pathogenesis of alzheimer's disease", j neurol neurosurg psychiatry, 1994, 57:419-425.
Rogers et at., "translation of the alzheimer amyloid precursor protein mRNA is up-regulated by interleukin-1 through 5'-untranslated region sequences", j biol chem, 274(10):6421-31, 1999.
Sambamurti et al., "Reduced Plasma A-beta 1-42 in a phase I clinical study of phenserine tartrate", 10th international conference on alzheimer's disease and related disorders, Madrid, Spain, Jul. 15-20, 2006, pp. 571-575.
Schmidt et al., "closed head injury—an inflammatory disease?", brain res brain res rev., Apr. 2005, 48(2):388-399.
Schmued et al., "Fluoro-Jade B: a high affinity fluorescent marker for the localization of neuronal degeneration", 2000, Brain Res, 874:123-130.
Schubert et al., "optimizing the sensitivity of the head thrust test for identifiying vestibular hypofunction", Feb. 2004, Phys Ther, 84(2):151-158.
Selwyn et al., "outcome after repetitive mild traumatic brain injury is temporally related to glucose uptake profile at time of second injury" j neurotrauma, Aug. 15, 2016, 33:1479-1491.
Shimohama, "apoptosis in alzheimer's disease—an update", apoptosis, 5(1):9-16, 2000.
Smith et al., "high tolerance and delayed elastic response of cultured axons to dynamic stretch injury", J Neurosci., Jun. 1, 1999, 19(11):4263-4269.
Smith et al., "therapy development for diffuse axonal injury", j neurotrauma, Mar. 1, 2013, 30:307-323.
Stuss et al., "subtle neuropsychological deficits in patients with good recovery after closed head injury", 1985, neurosurgery 17(1) Part 1:41-47.
Su et al., "elevated c-reactive protein levels may be a predictor of persistent unfavourable symptons in patients with mild traumatic brain injury: a preliminary study", brain, behavior, and immunity, 2014, 38:111-117.
Tombaugh, "trail making test a and b: normative data stratified by age and education", 2004, archives of clinical neuropsychology, 19:203-214.
Tsitsopoulos et al., "amyloid-B peptides and tau protein as biomarkers in cerebrospinal and interstitial fluid following traumatic brain injury: a review of experimental and clinical studies", Jun. 26, 2013, front neurol., 4(79):1-17.
Tweedie et al., "cognitive impairments induced by concussive mild traumatic brain injury in mouse are ameliorated by treatment with phenserine via multiple non-cholinergic mechanisms", PLoS One, Jun. 2, 2016, 11(6):e0156493, pp. 1-26.
Tweedie et al., "Exendin-4, a glucagon-like peptide-1 receptor agonist prevents mTBI-induced changes in hippocampus gene expression and memory deficits in mice", exp neurol, Jan. 2013, 239:170-182.
Tweedie et al., "Mild traumatic brain injury-induced hippocampal gene expressions: the identification of target cellular processed for drug development", J Neurosci Methods, [Epub ahead of print] 2016.
Uryu et al., "Repetitive mild brain trauma accelerates Abeta deposition, lipid peroxidation, and cognitive impairment in a transgenic mouse model of alzheimer amyloidosis", j neurosci, Jan. 15, 2002, 22(2):446-454.
Vriens et al., "The use of technetium tc 99m annexin v for in vivo imaging of apoptosis during cardiac allograft rejection", Nov. 1998, J Thorac Cardiovasc Surg. 116(5):844-853.
Walker et al., "how a single brain trauma may lead to alzheimer's disease", pp. 1-4, accessed on Apr. 19, 2018 via https://www.sciencedaily.com/releases/2012/07/120724171227.htm.
Wang et al., "diffuse traumatic axonal injury in the optic nerve does not elicit retinal ganglion cell loss", J Neuropathol Exp Neurol., Aug. 2013, 72(8):768-781.
Wilde et al., "diffusion tensor imaging of acute mild traumatic brain injury in adolescents", neurology, Mar. 18, 2008, 70(12):948-955.
Winblad et al., "Phenserine efficacy in alzheimer's disease", 2010, J. Alzh. Dis., 22:1201-1208.
Winston et al., "Prediction of conversion from mild cognitive impairment to dementia with neuronally derived blood exosome protein profile", 2016, alzheimers dement (asmt), 3:63-72.
Xu, "animal model of repetitive mild traumatic brain injury for human traumatic axonal injury and chronic traumatic encephalopathy", neural regen res. Nov. 2015, 10(11):1731-1732.
Yang et al., "post-trauma administration of the pifithrin-a oxygen analog improves histological and functional outcomes after experimental traumatic brain injury", exp neurol, Jul. 2015, 269:56-66.
Yang et al., "Post-traumatic administration of the p53 inactivator pifithrin-alpha oxygen analogue reduces hippocampal neuronal loss and improves cognitive deficits after experimental traumatic brain injury", Neurobiol Dis., 2016, 96:216-226.
Yu et al., "synthesis of novel phenserine-based-selective inhibitors of butyrylcholinesterase for alzheimer's disease", J. Med. Chem., 1999, 42(10):1855-1861.
Zhao et al., "the contribution of activated astrocytes to Abeta production: implications for alzheimer's disease pathogenesis", j neuroinflammation, 2011, 8:150.
Zhu et al., "abnormal mitochondrial dynamics in the pathogenesis of alzheimer's disease", j alzheimers dis. 2013, 33:s253-s2662.
Zhu et al., "novel p53 inactivators with neuroprotective action: syntheses and pharmacological evaluation of 2-imino-2,3,4,5,6,7-hexahydrobenzothiazole and 2-imino-2,3,4,5,6,7-hexahypdrobenzoxazole derivatives", j. med. Chem., 2002, 45(23):5090-5097.

* cited by examiner p<0.05 relative hypoxia (stroke) value
* p<0.05 relative to Normoxia (control) value

Brain region:
Dentate gyrus within the hippocampus

COMPOSITIONS AND METHODS FOR TREATING CONCUSSION

CROSS-REFERENCE TO RELATED APPLICATIONS

This application is a Continuation-in-part application of U.S. patent application Ser. No. 15/406,187, filed Jan. 13, 2017, entitled "COMPOSITIONS AND METHODS FOR TREATING CONCUSSION," which claims priority to U.S. Provisional Application Ser. No. 62/279,457, filed Jan. 15, 2016, entitled "METHOD FOR MEDICAL TREATMENT OF CONCUSSION" the entirety of each of which is incorporated herein by specific reference.

BACKGROUND

Technical Field

This disclosure generally relates to compositions and methods for treating concussion or other form of brain trauma, or for preventing the anecrotic cell death of neurons, or for treating the accompanying symptoms and functional impairments commonly associated with brain trauma and/or neuronal loss.

Related Technology

Brain trauma, such as traumatic brain injury (TBI), represent a significant and growing cause of disability and death worldwide, and is estimated to become the third largest cause of global disease burden by 2020. Every year, some 10 million individuals succumb to TBI events that can be broadly subdivided as either concussive or blast in origin. The former type of TBI is far more common, and is exemplified by events such as automobile accidents, full contact sporting injuries and falls in the young and, particularly, in the elderly. The latter type of TBI, generally resulting from a high-pressure shock wave from an explosive device, are a prevalent form of injury in modern combat arenas that primarily affect servicemen/women and civilians in active war zones. Head injuries provide a source of serious concern for obvious reasons. Additionally, medical evidence demonstrates that simple and not obviously injurious blows to the head can, as sub-concussive events, have the same or similar negative consequences as traumatic brain injuries and concussions. Sub-concussive events cause brain pathologies and/or neurodegeneration, which may potentially affect memory and contribute to the overall risk of developing late-onset chronic traumatic encephalopathy.

Neurological sequelae of TBI include shearing and compression of neuronal and vascular tissue that, in turn, initiate a secondary cascade of pathological events that cause further brain injury. Irrespective of the type of injury, mild to moderate TBI can lead to headaches, sleep disorders, and significant impairments across a broad range of brain functions such as attention, cognition, emotion and social behavior.

In addition to immediate TBI-induced physical injuries, ensuing secondary damage, and signature cognitive deficits, TBI is increasingly considered to be an important conduit to the development of chronic neurodegenerative disorders. In this regard, a strong association between TBI and the onset of dementia-related illness has been reported in US military veterans. This finding is of particular significance in the face of estimates that approximately 15% of all deployed military personnel receive a mild to moderate TBI of one form or another, with the total number of such injuries estimated as high as 320,000. TBI has also been associated with an increased likelihood of Parkinson's disease, particularly in the elderly. Within the US alone, it is estimated that at least 1.7 million people suffer a TBI event annually. Studies suggest that every year approximately 235,000 TBI victims require hospitalization that can, in the most severe instances, result in some 50,000 deaths annually. Indeed, at least 5.3 million Americans are presently believed to be living with long-term disabilities associated with a TBI, for which there is currently no effective pharmacological treatment.

Accordingly, there are problems in the area of compositions and treatments for the various forms of TBI and related neurodegenerative diseases that can be addressed.

BRIEF SUMMARY

Embodiments of the present disclosure solve one or more of the foregoing or other problems in the art with compositions and methods for treating and preventing brain traumas, including mitigating pathologies associated with degenerative brain diseases such as TBI and/or preventing anecrotic cell death in neurons. For example, at least one embodiment includes a composition having an active compound comprising one or more of phenserine, a phenserine metabolite, a phenserine prodrug, or combinations thereof and one or more pharmaceutically acceptable excipients. The composition includes the one or more pharmaceutically acceptable excipients being combined with the active compound to form an extended, controlled-release medicament that delivers a therapeutic concentration of the active compound over a period of time.

In at least one embodiment, the composition further includes a therapeutically acceptable daily dose of a second active compound, the second active compound comprising one or more of a steroid, a non-steroidal anti-inflammatory drug, acetaminophen, or combinations thereof and acting additively or synergistically with the active compound to treat brain traumas, including mitigating pathologies associated with degenerative brain diseases such as TBI and/or preventing anecrotic cell death in neurons.

Methods for preventing an onset of anecrotic cell death in neurons and an accompanying dementia from loss of neurons are also disclosed. For example, a method comprising administering a therapeutic dose of an active compound and a therapeutically acceptable daily dose of a second active compound, wherein the active compound comprises one or more of: phenserine, a phenserine metabolite, a phenserine prodrug, or combinations thereof, and wherein the second active compound comprises one or more of: a steroid, a non-steroidal anti-inflammatory drug, acetaminophen, or combinations thereof; and maintaining the therapeutic dose of the active compound and the therapeutically acceptable daily dose of the second active compound at therapeutically effective concentrations over a period of time to prevent the onset of anecrotic cell death in neurons and the accompanying dementia from loss of neurons.

Accordingly, compositions and methods for treating and preventing brain traumas, including the accompanying symptoms and functional impairments commonly associated with neuronal loss are disclosed.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by references to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1A:
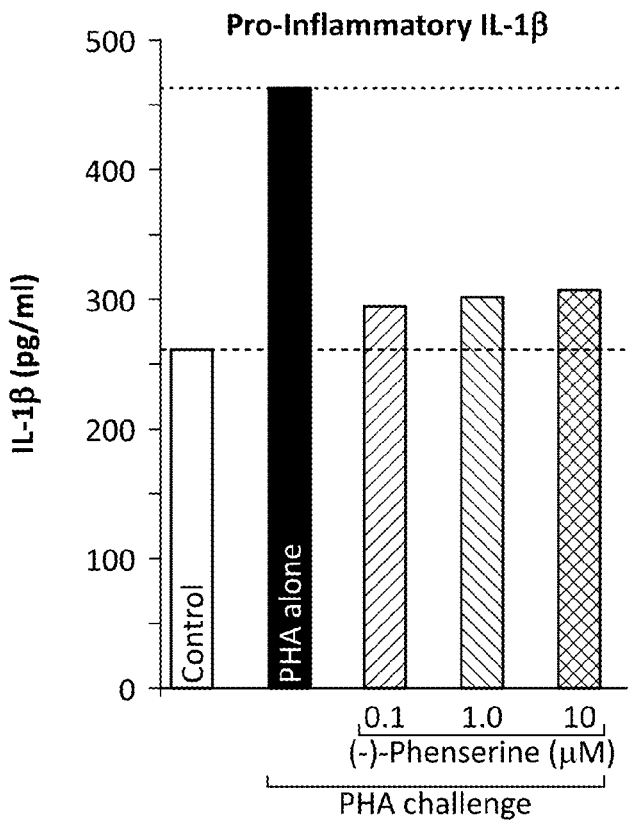
FIGS. 1A-1B illustrate effects of phenserine on pro-inflammatory and anti-inflammatory cytokine production.

Before describing various embodiments of the present disclosure in detail, it is to be understood that this disclosure is not limited to the parameters of the particularly exemplified systems, compositions, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments, and is not necessarily intended to limit the scope of the claimed invention.

Overview of Brain Traumas and Treatment Methods

As provided above, brain traumas such as TBI represent a significant and growing cause of disability and death worldwide. For example, an estimated 1.5 million people visit emergency rooms annually for head injuries, an estimated 1.6 million to 3.8 million sports-related injuries occur yearly in the United States, and it is estimated that as many as 10-20% Iraq war veterans have suffered some sort of head injury.

Concussions, or mild traumatic brain injury (mTBI), are common. Most affected individuals appear to recover and return to sports or other activities where the original concussion occurred. However, recent evidence has suggested that physicians do not allow adequate time for recovery. By 3 months after injury, 30-50% of patients will still have symptoms of mTBI. Even well-recovered patients will be susceptible to periodic impairments under conditions of physiological or psychological stress. Increased sensitivity to moderate alcohol, sleep deprivation, lengthy travel schedules, and workload can become long lasting, and if present for over 2 years, is often regarded as permanent. At 1 year after injury, 10-15% of mTBI patients have not recovered, and some feel worse. Persistent Post-Concussion Syndrome can develop in up to 15% of this high-risk group. Some patients, especially the elderly or those with demanding jobs and/or predisposing personalities, may always be aware of deficits in performance.

Examples of clinical pathologies from brain trauma—such as those caused by traumatic brain injury, concussion, and sub-concussive injury—include loss of consciousness, feeling dazed, disorientation, cognitive losses, mood changes, executive function disorders, headaches, and sleep disturbances. In some instances these pathologies are caused by shearing and compression of neuronal and vascular tissue that, in turn, initiates a secondary cascade of pathological events that generate a hostile environment in the brain marked by the release of excitatory amino acids (glutamate excitotoxicity), free radical accumulation, calcium influx, oxidative damage, activated proteases, inflammatory responses by non-neuronal brain cells, and/or blood-brain barrier dysfunction—which allows the entry of inflammatory cytokines and chemokines that initiate and/or promote inflammation. In many instances, the hostile environment generated in the brain leads to neuronal cell loss through apoptosis or other anecrotic cell death pathways. Further, neuronal cell loss is associated with a variety of neurodegenerative disorders such as Parkinson's and/or Alzheimer's diseases.

In other words, the brain trauma, itself, and/or the cascade of pathologies resulting from the hostile environment created thereby, promotes, among other things, a loss of neurons—particularly via anecrotic cell death—which plays a large role in the pathological presentation and progression of disease. For example, neuronal dysfunctions such as synaptic losses and anecrotic cell death lead to the clinical cognitive and functional pathology following TBI (e.g., concussion and sub-concussive injuries) as well as following the pathological processes present in neurodegenerative diseases (e.g., Parkinson's and Alzheimer's). However, no drugs are currently available to mitigate the neurodegenerative or neuropathological sequelae from these various brain traumas, and particularly, no drugs are available for preventing anecrotic cell death of neurons that are situated within a hostile environment.

Due to the lack of drugs capable of arresting, mitigating, or slowing the development of brain pathologies after head injuries, patients with these conditions are prescribed physical and mental rest. This often includes restricted physical and mental activities, particularly in view of evidence that patients recovering from concussion have been shown to be at risk of serious immediate and/or long-term consequences should a second concussive event occur. This creates the need for special vigilance and management to ensure that any neuropathology awakened by an initial TBI, concussion, or sub-concussive injury has completely subsided before the patient returns to normal activity.

As an additional consequence to the striking lack of drugs capable of arresting, mitigating, or slowing the development of brain pathologies after head injuries and the deleterious sequelae that result therefrom, social changes have been implemented to reduce the risk of TBI and possible sequelae (such as chronic traumatic encephalopathy), including attempts to mitigate the severity of head injuries. Some exemplary ways this has been implemented include using protective equipment during sports and recreation, using seat belts while driving, making homes safe for both children and adults, maintaining strength and agility, and raising awareness of concussions and head injuries. Unfortunately, none of these prevent all clinically important brain traumas and their complications.

Advances in our understanding of the molecular mechanisms that regulate the health and survival of neurons in neurodegenerative conditions has allowed identification of key biochemical cascades linked to neuronal dysfunction and cellular demise that may be amenable to pharmacologic intervention. Prior studies using pharmacological tools, such as anti-apoptotic p53 inhibitors, indicate that neuronal cell death occurring in the secondary phase of injury can be halted to thereby mitigate cognitive deficits; however, such agents are not readily clinically translatable. In contrast, clinically translatable drugs focused towards mechanisms shared between neurodegenerative disorders and TBI have yet to provide unequivocal efficacy profiles supportive of clinical approval.

Accordingly, treatment regimens as well as protective interventions, that include a drug capable of mitigating and/or preventing brain pathologies responsible for immediate and long-term neurodegenerations, induced neuropathologies, symptoms, pathologies, functional impairments, and disabilities resulting from brain traumas (e.g., concussions, sub-concussive brain injuries, and neurodegenerative diseases such as Parkinson's and Alzheimer's) is desirable.

In one or more embodiments, the disclosed compositions and/or methods suppress the severity of neuropathological degenerative, cognitive, functional, and other impairments and/or pathologies following brain trauma. This may in some embodiments be the result of preventing anecrotic cell death of neurons induced by brain trauma, or it may, additionally, or alternatively, be the result of mitigating at least a portion of the cascade of pathologies associated with the brain trauma. For example, compositions and treatment methods disclosed herein utilize an extended, controlled-release formulation of phenserine to mitigate one or more pathologies following brain trauma and/or at least a portion of the cascade of pathologies associated therewith, which ameliorates and/or protects against the negative consequences and sequelae associated with brain traumas such as TBI and mTBI. In some embodiments, compositions and treatment methods of the present disclosure may additionally include concomitant treatment with an anti-inflammatory drug that acts additively or synergistically with phenserine to, in some embodiments, treat TBI, mTBI, and/or sub-concussive injury and/or mitigate the pathologies associated with brain trauma that lead to progression into the clinical disease state. Additionally, or alternatively, the compositions and treatment methods of the present disclosure may prevent the onset of anecrotic cell death in neurons. In some embodiments, the foregoing extended, controlled-release formulations of phenserine with or without an additional anti-inflammatory drug can be used to treat neurodegenerative conditions such as Parkinson's and Alzheimer's.

Compositions for Preventing Anecrotic Cell Death in Neurons and/or Mitigating Pathologies Following Brain Trauma or the Cascade of Pathologies Associated Therewith The present disclosure provides compositions for mitigating one or more pathologies following brain trauma or at least a portion of a cascade of pathologies associated therewith. In some embodiments, compositions are used to treat TBI, concussion, and/or sub-concussive injuries. Accordingly, one or more embodiments of the present disclosure provide compositions for mitigating the effects of anecrotic cell death in neurons and/or suppressing the neuropathological degenerative, clinical cognitive, and/or other impairments of the brain following brain trauma. In at least one embodiment, a composition includes, among other things, an active compound that includes phenserine. Phenserine is of special interest for the proposed uses since, among other things, long-term administrations to humans has proven safe.

While phenserine has been previously utilized to treat Alzheimer's Disease, its previous applications have focused on its properties as an acetylcholinesterase inhibitor and has exclusively been provided in immediate release formulations. This form of immediate drug release has been lauded as advantageous over other forms.

Existing data support a short (2.0-2.5 hour maximum) elimination half-life for phenserine and for its metabolites while the acetylcholinesterase activity remains higher, relative to phenserine and/or phenserine metabolite concentration, over a longer period due to a slow rate of drug/enzyme dissociation. The rapid clearance of drug and prolonged steady-state acetylcholinesterase inhibition was previously shown to be beneficial due to the lower risks of drug accumulation and more physiological patterns of support for brain cholinergic functioning. On the contrary, however, phenserine in immediate release formulation has not been shown to provide (1) a sufficiently long duration of drug or active metabolite steady-state concentrations, or (2) persisting beneficial pharmacological effects even after elimination of drug and metabolites. As a result, immediate release formulations caused patients to go 14 or more hours daily without drug or metabolites present in or even near therapeutic concentrations.

Accordingly, the dosing of phenserine in earlier studies in humans could not be explained since attempts at explanation focused on phenserine without consideration of metabolites. In all species and tissues tested following oral administrations, phenserine reached peak concentration levels at 1.5-2 hours and rapidly declined by 4 hours or sooner to levels less than 1 ng/mL. Peak phenserine plasma concentrations estimated in the single digit range and subsequent lower concentrations are inconsistent with the required levels of pharmacological activity as determined by its tested estimated $IC_{50}$=24-26 nM, which had been demonstrated for anticholinesterase activity.

To address this issue, phenserine metabolism was analyzed in different mammalian species, where it was unexpectedly found that the principal actions of phenserine occur, not from its inherent molecular properties alone but because of its rapid metabolism, in the main as a first pass effect in liver following oral administrations to its (−)-N1, N8-bisnorphenylcarbamoyleseroline, (−)-N1-norphenylcarbamoyleseroline, and/or (−)-N8-norphenylcarbamoyleseroline pharmacologically active metabolites. The metabolites (−)-N1-norphenylcarbamoyleseroline, and norphenylcarbamoyleseroline are then rapidly, but not completely, metabolized in all mammalian species tested, including humans, to (−)-N1, N8-bisnorphenylcarbamoyleseroline. Much of the acetylcholinesterase activity observed after administration of phenserine in humans can be ascribed, partly or wholly, to the (−)-N1, N8-bisnorphenylcarbamoyleseroline metabolite, although each of the other metabolites and phenserine itself provide important levels of activities at different times following oral administration.

The metabolism of phenserine to (−)-N1, N8-bisnorphenylcarbamoyleseroline, with an estimated $IC_{50}$=100 nM provides measurable activity in the peripheral blood. Whereas phenserine has a high brain:blood partition (approx. 8:1) but is rapidly metabolized in blood, the lower brain:blood partition of each of its metabolites (N1-norphenylcarbamoyleseroline: approx. 4:1, N8-norphenylcarbamoyleseroline: approx. 6:1, and N1, N8-bisnorphenylcarbamoyleseroline: approx. 1.3:1) allows both the primary compound and its metabolites to contribute to the brain pharmacological activity, such as preventing anecrotic cell death of neurons, which is achieved following phenserine administration. Accordingly, in some embodiments, an $IC_{50}$ in the range of 24-100 nM is used to establish dosing parameters for compositions and methods of treatments disclosed herein.

Particularly when utilized for mitigating pathologies subsequent to brain trauma and/or for preventing anecrotic cell death in neurons, it is advantageous to prolong exposure of brain cells and neurons to therapeutic concentrations of phenserine over periods of time, in some embodiments, that are greater than what could be achieved through immediate release formulations. Accordingly, extended, controlled-release formulations disclosed herein have been developed to address these problems.

Additionally, or alternatively, extended, controlled-release formulations disclosed herein provide the advantage of delivering a more consistent therapeutic concentration of active compound to the brain as opposed to the peaks and troughs of drug concentrations that would result in serially dosing an immediate release formulation. Further, in some embodiments, by providing sustained levels of drug in the brain, extended release formulations allow the brain and other body systems to accumulate to higher concentrations of drug. This accumulation was not available with immediate dosing, particularly as seen in previous investigations of single immediate release formulation 15 mg doses. The rapid metabolism of the drug led to no appreciable level of drug being present at subsequent clinically practical dosing opportunities (usually no sooner than six hours), and thus, no accumulated drug concentrations were attainable from multiple immediate release formulation doses.

Stated another way, one advantage of the extended, controlled release medicaments disclosed herein is that a threshold level of phenserine is maintained in the body, which provides previously unrealized neuroprotective and pathological mitigation effects. These benefits have been wholly unappreciated for treating brain traumas, including, for example, for treating TBI, mTBI, and sub-concussive injury as well as in treating neurodegenerative disorders such as Alzheimer's and Parkinson's diseases. This is in contrast to previous formulations of phenserine used to treat Alzheimer's disease. Previous treatment methods and compositions were focused on maintaining the acetylcholinesterase inhibition activity of the drug over time, without regard to the levels of phenserine in the system. Due to the disparity between the acetylcholinesterase inhibitory activity and the presence of the phenserine (i.e., phenserine is quickly metabolized and removed from the system, whereas the acetylcholinesterase activity lingers for a prolonged period in the absence of phenserine), any extended release formulation previously conceived using phenserine to treat Alzheimer's disease or other neurodegenerative conditions would be fundamentally different than those disclosed herein. Instead of providing a spike of phenserine followed by a period of absence with a subsequent spiked dosage, the present disclosure provides compositions and methods of treatment that provide a concentration of phenserine consistently above a threshold amount, thereby ensuring continual presence of the drug.

Additional problems of sub-therapeutic concentrations of phenserine provided by immediate release formulations are addressed by the extended, controlled-release formulations disclosed herein. For example, based on the low bioavailability of phenserine (below 25%), a relatively insignificant variation (e.g., 5-10%) provides large (possibly 50%) relative differences in drug concentrations across individuals (see, for example, FIGS. 13 & 15). With a readily bioavailable compound, for example of 85-90% bioavailability, inter-subject variability of 10% would be much less consequential for target drug concentrations.

Therefore, in some embodiments, phenserine provides desirable pharmacokinetic and pharmacodynamic properties and may be practically used as both a drug and a backbone prodrug, particularly within extended, controlled-release formulations.

In some embodiments, an extended, controlled release formulation delivers between about 0.05-5 mg/h, preferably about 1-5 mg/h, into the blood to achieve steady-state pharmacological action in the brain. In at least one embodiment, therapeutically effective brain concentrations of active compound are provided by administering phenserine in therapeutically acceptable (e.g., daily) doses ranging from about 0.05-5 mg/hour, preferably about 1.25-2.5 mg/hr (over the relevant treatment period, e.g., per day) or about 1.2-120 mg/day, preferably 30-60 mg/day (over the relevant treatment period), either alone or in combination with aspirin and/or other second active drug(s) disclosed herein (e.g., a steroid, an NSAID, acetaminophen, or combinations thereof).

In other embodiments, phenserine (with or without a second active drug) is administered (or released from the formulation) in doses ranging from or between about 0.005-10 mg/hour, about 0.05-10 mg/hour, about 0.5-10 mg/hour, about 1-10 mg/hour, 1.5-10 mg/hour, 2-10 mg/hour, 2.5-10 mg/hour, 3-10 mg/hour, 4-10 mg/hour, 5-10 mg/hour, about 0.005-5 mg/hour, about 0.05-5 mg/hour, about 0.5-5 mg/hour, about 1-5 mg/hour, about 1.5-5 mg/hour, about 2-5 mg/hour, about 2.5-5 mg/hour, about 3-5 mg/hour, about 4-5 mg/hour, about 0.005-4 mg/hour, about 0.05-4 mg/hour, about 0.5-4 mg/hour, about 1-4 mg/hour, about 1.5-4 mg/hour, about 2-4 mg/hour, about 2.5-4 mg/hour, about 3-4 mg/hour, about 0.005-3 mg/hour, about 0.05-3 mg/hour, about 0.5-3 mg/hour, about 1-3 mg/hour, about 1.5-3 mg/hour, about 2-3 mg/hour, about 2.5-3 mg/hour, about 0.005-2.5 mg/hour, about 0.05-2.5 mg/hour, about 0.5-2.5 mg/hour, about 1-2.5 mg/hour, about 1.5-2.5 mg/hour, about 2-2.5 mg/hour, about 0.005-2 mg/hour, about 0.05-2 mg/hour, about 0.5-2 mg/hour, about 1-2 mg/hour, about 1.5-2 mg/hour, about 0.005-1.5 mg/hour, about 0.05-1.5 mg/hour, about 0.5-1.5 mg/hour, about 1-1.5 mg/hour, about 0.005-1 mg/hour, about 0.05-1 mg/hour, about 0.5-1 mg/hour, less than about 10 mg/hour, less than about 5 mg/hour, less than about 4 mg/hour, less than about 3 mg/hour, less than about 2.5 mg/hour, less than about 2 mg/hour, less than about 1 mg/hour, greater than about 0.005 mg/hour, greater than about 0.05 mg/hour, greater than about 0.5 mg/hour, greater than about 1 mg/hour, greater than about 1.5 mg/hour, greater than about 2 mg/hour, greater than about 2.5 mg/hour, greater than about 3 mg/hour, greater than about 4 mg/hour, or greater than about 5 mg/hour, and/or combinations or intermediate values or ranges of any of the foregoing ranges, maximums, or minimums, any of which may be administered with or without the second active drug (over the relevant treatment period, e.g., per day).

In other embodiments, phenserine is administered (or released from the formulation) in doses ranging from or between about 0.01-120 mg/day, about 0.05-120 mg/day, about 0.1-120 mg/day, about 1-120 mg/day, about 3-120 mg/day, about 5-120 mg/day, about 10-120 mg/day, about 5-90 mg/day, about 5-80 mg/day, about 5-70 mg/day, about 5-60 mg/day, about 5-50 mg/day, about 5-40 mg/day, about 5-30 mg/day, about 5-20 mg/day, about 5-15 mg/day, about 0.5-15 mg/day, about 15-60 mg/day, about 15-50 mg/day, about 20-50 mg/day, about 30-50 mg/day, about 30-60 mg/day, about 30-70 mg/day, about 40-80 mg/day, about 30-45 mg/day, about 45-60 mg/day, about 30 mg/day, about 45 mg/day, about 60 mg/day, about 80 mg/day, about 90 mg/day, about 100 mg/day, less than about 200 mg/day, less than about 150 mg/day, less than about 120 mg/day, less than about 100 mg/day, less than about 80 mg/day, less than about 70 mg/day, less than about 60 mg/day, less than about 50 mg/day, less than about 40 mg/day, less than about 30 mg/day, less than about 20 mg/day, less than about 15 mg/day, less than about 10 mg/day, less than or equal to about 5 mg/day, less than or equal to about 4 mg/day, less than or equal to about 3 mg/day, less than or equal to about 2 mg/day, less than or equal to about 1 mg/day, less than or equal to about 0.5 mg/day, less than or equal to about 0.05 mg/day, greater than about 5 mg/day, greater than about 10 mg/day, greater than about 15 mg/day, greater than about 20 mg/day, greater than about 30 mg/day, greater than about 40 mg/day, greater than about 50 mg/day, greater than about 60 mg/day, greater than about 70 mg/day, greater than about 80 mg/day, greater than about 90 mg/day, greater than about 100 mg/day, greater than about 125 mg/day, greater than about 150 mg/day, and/or combinations or intermediate values or ranges of any of the foregoing ranges, maximums, or minimums, any of which may be administered with or without the second active drug (over the relevant treatment period, e.g., per day).

Although implicit in the foregoing, similar and/or substantially the same beneficial therapeutic effects observed with phenserine treatment can also be provided by administering one or more phenserine metabolites in doses ranging from any of the dosage ranges disclosed above with respect to phenserine.

In some embodiments, phenserine can be administered (or released from the formulation) in a therapeutic dosage or concentration (sufficient to be therapeutic, alone). In other embodiments, phenserine can be administered (or released from the formulation) in a therapeutic dosage or concentrations (insufficient to be therapeutic, alone).

Additionally, or alternatively, phenserine can be combined with an anti-inflammatory drug that is provided in a therapeutically acceptable daily dose and which acts additively or synergistically with phenserine to mitigate one or more pathologies following brain trauma and/or prevent the onset of anecrotic cell death in neurons. In at least one embodiment, a composition includes both the anti-inflammatory drug and phenserine, each provided at concentrations in the composition that if administered individually would provide a therapeutic benefit. In at least one embodiment, formulations containing both the anti-inflammatory drug and phenserine include formulations where the concentration of phenserine provided in the formulation would result in sub-therapeutic concentrations of phenserine in the absence of the anti-inflammatory drug, yet when administered with the anti-inflammatory drug results in therapeutic effects observed in higher concentrations of phenserine alone (e.g., therapeutic concentrations of phenserine). Nonetheless, it will be appreciated that an anti-inflammatory drug may be provided in compositions where the concentration of phenserine would yield therapeutic concentrations in the absence of the anti-inflammatory drug.

In at least one embodiment, the anti-inflammatory drug is a non-steroidal anti-inflammatory drug (NSAID), such as ibuprofen. In at least one embodiment, the anti-inflammatory drug is acetylsalicylic acid—commonly referred to as aspirin. In at least one embodiment, the anti-inflammatory drug is a steroid such as dexamethasone. In one or more embodiments, the second active drug is provided and/or maintained at a therapeutically acceptable daily dose, as defined below. In one embodiment, the anti-inflammatory drug is acetaminophen.

In one embodiment, the therapeutically acceptable daily dose of the anti-inflammatory drug may be maintained for any duration of treatment concurrent with or separate from administration and/or treatment with phenserine. In at least one embodiment, the anti-inflammatory drug is maintained at a therapeutically acceptable daily dose for the duration of the treatment period. The treatment period may be any duration prescribed by a physician and is, in some embodiments, an indefinite period of time.

It should be appreciated that the compositions and formulations disclosed herein can be administered before a brain trauma event as a prophylactic measure to mitigate one or more pathologies following the brain trauma event (e.g., the onset of anecrotic cell death in neurons or the pathologies culminating therein or associated therewith). In some embodiments, the prophylactic treatment is given one day prior to a brain injury event. In other embodiments, the prophylactic treatment is given multiple days to weeks before the brain injury event. In yet other embodiments, the prophylactic treatment is given without induction of a brain injury event. For example, an individual may present with a high risk of experiencing a brain trauma event, and an attending physician prescribes a prophylactic treatment regimen that includes one of the foregoing compositions with the intention of mitigating pathologies subsequent to brain trauma, should it occur, and/or preventing anecrotic cell death in neurons.

Alternatively, the compositions and formulations disclosed herein can be administered after a brain injury event or discovery of brain trauma for ameliorating the symptoms and negative consequences or possible sequelae associated with brain traumas.

Oral and other routes can be used for administering phenserine as well as for administering the anti-inflammatory drug. Accordingly, in some embodiments, the compositions of the present disclosure are administered orally (or sublingually) in the form of a tablet, capsule, pill, liquid suspension, or in any other forms known in the art. Additionally, or alternatively, the compositions of the present disclosure may be administered in the form of a gel or nanoparticle or microparticle or polymer formulation for delayed release at sites of inflammation or brain trauma, or the compositions may be administered intravenously, subcutaneously, transdermally, nasally, or intramuscularly.

In a preferred embodiment, one or more of the disclosed compositions are administered orally in a slow release dosage formulation. For example, an extended, controlled-release formulation provided as a medicament includes an active compound having one or more of phenserine, its metabolites, a phenserine prodrug, or combinations thereof combined with a pharmaceutically acceptable excipient. The extended, controlled-release medicament releases the active compound at a given rate (e.g., between 0.1 mg and 5 mg/h) and may do so over a period of time (e.g., 24 hours).

Pharmaceutically acceptable excipients include any pharmaceutical excipient known in the art and which can be combined with the active compound(s) of the disclosed compositions to control release of the active compound(s). In some embodiments, the pharmaceutically acceptable excipient includes a wax formulation (e.g., hydrogenated castor oil). Additionally, or alternatively, the pharmaceutically acceptable excipient includes hydrophilic polymers (e.g., hydroxypropyl cellulose).

In some embodiments, the concentration of medicament released is greater than about 0.1 mg/h, greater than about 0.5 mg/h, greater than about 1 mg/h, greater than about 2 mg/h, greater than about 3 mg/h, greater than about 4 mg/h, greater than about 5 mg/h, greater than about 10 mg/h, less than about 15 mg/h, less than about 10 mg/h, less than about 5 mg/h, less than about 4 mg/h, less than about 3 mg/h, less than about 2 mg/h, less than about 1 mg/h, less than about 0.5 mg/h, or provided and dispensed in concentration ranges defined by any of the foregoing.

In some embodiments, the period of time in which the medicament releases active compound(s) is about 6 hours, about 8 hours, about 12 hours, about 18 hours, or about 24 hours, or it may be a range of times including, for example, about 8-12 hours, about 12-16 hours, about 18-21 hours, or similar. It should be appreciated that the period of release, the rate of release, and the total daily dose of active compound may include any combination of the periods of release, rates of release, and total daily dosages and may be administered in any of the disclosed forms, preferably in the form of an extended, controlled-release tablet or capsule.

It will be appreciated that in some embodiments, the medicament is administered intramuscularly and/or subcutaneously and may release active compound over longer periods, such as five days to one week or more.

In some embodiments, maintaining a therapeutic dose of the active compound at therapeutically effective concentrations over a period of time includes maintaining the therapeutic dose over a treatment period. In at least one embodiment, the treatment period is any duration of time prescribed by a licensed medical professional (e.g., the prescribing and/or treating physician) for the treatment of the brain trauma. For example, the treatment period for a concussion (or other TBI) may be for at least one week, at least two weeks, at least three weeks, at least four weeks, at least five weeks, at least six weeks, at least seven weeks, at least eight weeks, at least three months, at least four months, at least five months, at least six months, or longer. The treatment period for a concussion (or other TBI) may be patient specific and related to the severity and/or history of concussion (or other TBI) in said patient. In some embodiments, the treatment period for concussion is the duration of time that is required to return the brain to steady state conditions. This includes, for example, a return of inflammatory markers (e.g., C-reactive protein, increased white blood cell count, the presence of pro-inflammatory cytokines or chemokines, or other pro-inflammatory markers known in the art) to a steady state or pre-concussive state.

Additionally, or alternatively, biomarkers and/or diagnostic criteria of anecrotic cell death may be monitored to determine the efficacy of treatment and/or as a biomarker/diagnostic criterion of anecrotic cell death in humans. Cellular changes observed to occur during anecrotic cell death (e.g., apoptosis) include the externalization of the phospholipid phosphatidylserine (PS). Specifically, the translocation of PS, from the inner membrane to the outer membrane of cells, is used routinely as a marker of the early stages of apoptosis. The antibody Annexin V binds strongly with PS, and its detection has been widely used for imaging of anecrotic cell death (e.g., apoptosis) both in cellular studies and in vivo, including in humans. Accordingly, imaging of externalized PS using Annexin V is one non-limiting example of (or means for) monitoring hallmarks of anecrotic cell death to determine the efficacy of treatment and/or as a biomarker/diagnostic criteria for determining anecrotic cell death in humans.

It will be appreciated that the use of Annexin V is just one non-limiting example of monitoring a marker of anecrotic cell death in humans. In some embodiments, cyclooxygenase-2 can additionally or alternatively be monitored to determine efficacy of treatment and/or completion of the treatment period. Other biomarkers, as known in the art, can also or alternatively be used (e.g., monitored) as an indication of anecrotic cell death or mitigation thereof. Thus, one of skill in the art can demonstrate anecrotic cell death through a variety of markers, means, assays, etc.

It should be appreciated that the therapeutically effective concentration of the phenserine may change throughout the treatment period. In some embodiments, the therapeutically effective concentration is prescribed at higher concentrations at or close to the onset of treatment and tempered to a lower concentration as the treatment period is prolonged. For example, a therapeutically effective concentration may be 5 mg/h phenserine in the blood at or near the onset of the treatment period, which is maintained for one or more weeks (such as two or more, three or more, four or more, etc.). At a predetermined interval following the initial treatment period, or at a time determined by the prescribing and/or treating physician, the therapeutically effective concentration may be lowered to, for example, at least 2 mg/h phenserine released in the blood. It will be appreciated that the foregoing therapeutically effective concentrations are exemplary, and any of the concentrations described herein may be substituted where appropriate. Accordingly, it is possible that a treatment period may begin with a period of time where a lower concentration of phenserine is prescribed as the therapeutically effective concentration followed by a higher concentration of active compound being prescribed over a subsequent treatment interval.

As a non-limiting example, a physician may prescribe a relatively high concentration of phenserine shortly after diagnosing a patient with concussion and subsequently prescribe a lower concentration of phenserine weeks after the initial diagnosis and treatment. The modular treatment regimen may allow the physician to initially treat the concussion and/or pathologies associated therewith with higher concentrations of phenserine followed by a lower (yet still therapeutically effective concentration) of phenserine to, for example, protect neurons from the onset of anecrotic cell death in the aftermath of an unresolved or partially resolved hostile environment in the brain following the brain trauma or the potential onset of anecrotic cell death in the event the patient experiences a secondary brain trauma. In the foregoing example, the phenserine is provided in an extended, controlled-release medicament such that the therapeutic concentrations of phenserine are maintained throughout the treatment periods.

As an additional non-limiting example, a physician may prescribe a relatively low concentration of phenserine to an individual at future risk of brain trauma (e.g., an athlete) followed by a relatively higher concentration of phenserine following the patient experiencing a head injury, concussive event, or otherwise presenting with a brain trauma.

In embodiments where phenserine is the active compound, negative consequences (e.g., vomiting, diarrhea, nausea, etc.) have been observed in patients exposed to an immediate release dose of 20 mg. Thus, it will be appreciated that formulations of the extended, controlled-release medicament will, in some embodiments, deliver dosages of phenserine or its metabolites below the threshold where negative consequences are observed in the patient. In other embodiments, a dosage of phenserine or its metabolites provided in an extended, controlled-release medicament are provided at a dosing concentration that leads to some negative consequences, where the beneficial effects of the active compound outweigh the negative consequences, as determined by a licensed medical professional. For example, using testing methods available in medical clinical laboratories, blood cholinesterase activities or metabolite concentrations can be monitored as estimators of brain concentrations, and based on that information, dosing can be managed by monitoring a patient's blood cholinesterase activities to ensure a therapeutic dose of the active compound(s) is being provided to the brain.

In at least one embodiment, the extended, controlled-release medicament maintains a blood plasma concentration of active compound that that results in a brain concentration of the active compound (e.g., phenserine and its metabolites) between 25 nM-250 nM. In some embodiments, the extended, controlled-release medicament maintains a blood plasma concentration of active compound that results in a brain concentration of active compound between 1 nM-500 nM, 5 nM-500 nM, 10 nM-500 nM, 50 nM-500 nM, 100 nM-500 nM, 200 nM-500 nM, 300 nM-500 nM, 400 nM-500 nM, 1 nM-400 nM, 1 nM-300 nM, 1 nM-200 nM, 1 nM-100 nM, 1 nM-50 nM, 1 nM-10 nM, 25 nM-400 nM, 25 nM-300 nM, 25 nM-200 nM, 25 nM-100 nM, 25 nM-75 nM, 25 nM-50 nM, 50 nM-200 nM, 50 nM-300 nM, 50 nM-400 nM, 100 nM-200 nM, 100 nM-250 nM, 100 nM-300 nM, 100 nM-400 nM, 100 nM-500 nM, 200 nM-250 nM, 200 nM-300 nM, 200 nM-400 nM, 200 nM-500 nM, or 250 nM-500 nM.

Additionally, or alternatively, the extended, controlled-release medicament maintains a blood plasma concentration of active compound that results in a brain concentration of the active compound above a lower threshold such as at greater than 1 nM, greater than 5 nM, greater than 10 nM, greater than 25 nM, greater than 50 nM, greater than 100 nM, greater than 200 nM, greater than 300 nM, or greater than 400 nM. In some embodiments, the lower threshold is determined by the severity of brain trauma and/or other reasons such as the drug being administered as a prophylactic treatment. For example, a prophylactic treatment may have a lower threshold than a treatment regimen following TBI or mTBI. As an additional, non-limiting example, the threshold plasma concentration of phenserine may be lower.

Methods for Mitigating Pathologies Subsequent to Brain Trauma and/or for Preventing Anecrotic Cell Death in Neurons The present disclosure provides methods to treat the symptoms and functional impairments that result from brain trauma (e.g., anecrotic cell death of neurons induced by head injury, concussion, sub-concussion, other neurodegenerative diseases including but not limited to Parkinson's disease, Alzheimer's disease, or other brain traumas as defined herein). In some embodiments, methods are provided for dosing a patient who has suffered a source of brain trauma or who is at risk of brain trauma. An exemplary method includes the steps of dosing a patient who has suffered or is at risk of suffering a traumatic brain injury, concussion, or sub-concussive injury with phenserine or one of its metabolites, alone or combined with an anti-inflammatory drug, and maintaining said dosage at a level and over a period sufficient to create therapeutic concentrations of phenserine and/or its metabolites in the brain. In some embodiments the method additionally includes administration of an anti-inflammatory drug, whereby following the withdrawal from treatment with the drug(s) the patient escapes or has reduced the immediate consequences from the brain trauma and exhibits a reduced risk of long-term sequelae such as chronic traumatic encephalopathy.

In some embodiments, the methods for mitigating one or more pathologies following brain trauma or at least a portion of a cascade of pathologies associated therewith include identifying an individual who has suffered or is at risk of brain trauma. A physician or other licensed medical professional may identify/diagnose the individual using one or more current or former diagnostic criteria. For example, the American Congress of Rehabilitation Medicine defines the criteria for concussion (also known as mild traumatic brain injury) as an individual having had a traumatically induced physiologic disruption of brain function, as manifested by one or more of: 1) any loss of consciousness up to 30 min, 2) any loss of memory for events immediately before or after the accident for as much as 24 h, 3) any alteration of mental state at the time of the accident, (e.g., feeling dazed, disoriented, or confused), or having 4) focal neurologic deficits that might or might not be transient, but where the severity of the injury does not exceed criteria for moderate and severe traumatic brain injury which are i) loss of consciousness exceeding 30 min, ii) posttraumatic amnesia longer than 24 h, or iii) a Glasgow Coma Scale score falling below 13 after 30 min. Additionally, or alternatively, an individual may be diagnosed with concussion using any other current diagnostic criteria such as the Glasgow Coma Scale, the Standardized Assessment of Concussion, Sport Concussion Assessment Tool 3, other neurological and cognitive testing by a physician (including or excluding the use of imaging tests such as computerized tomography or magnetic resonance imaging). In some embodiments, the criteria for sub-concussive injury are a history of head injury not meeting criteria for concussion or other traumatic brain injury.

In some embodiments, a post-concussive syndrome can occur following concussion. As a non-limiting example, this may consist of a history of head trauma with loss of consciousness preceding symptom onset by a maximum of 4 weeks and the presence of symptoms in 3 or more of the following symptom categories: 1) headache, dizziness, malaise, fatigue, noise intolerance; 2) irritability, depression, anxiety, emotional lability; 3) subjective concentration, memory, or intellectual difficulties without neuropsychological evidence of marked impairment; 4) insomnia; 5) reduced alcohol tolerance; and 6) preoccupation with above symptoms and fear of brain damage with hypochondriacal concern and adoption of sick role.

In at least one embodiment, methods for mitigating one or more pathologies following brain trauma or at least a portion of a cascade of pathologies associated therewith (e.g., include monitoring the effectiveness of drug intervention). This may include, for example, assessing and/or monitoring one or more signs and symptoms of brain trauma, including: headache, nausea, vomiting, blurred or double vision, seeing stars or lights, balance problems, dizziness, sensitivity to light or noise, tinnitus, drowsiness, fatigue or lethargy, irritability, depression, anxiety, sleeping more than usual, difficulty falling asleep, feeling "slowed down," "in a fog" or "dazed," difficulty concentrating, and impaired memory.

Additionally, or alternatively, methods for mitigating one or more pathologies following brain trauma or at least a portion of a cascade of pathologies associated therewith (e.g., preventing anecrotic cell death in neurons) include tailoring an extended, controlled-release formulation to the individual based on their personal metabolic profile (or other relevant factors). In some embodiments, this provides the benefits of rendering the extended, controlled-release formulation functional, predictable, and safe for individual patients who may each be prescribed formulations at differing effective concentrations. In at least one embodiment, assays of acetylcholinesterase activities in cerebrospinal fluid and/or blood can be used to monitor the nanomolar concentrations of phenserine and/or its metabolites in the brain. Because of drug pharmacokinetics and clinical intrusiveness, the use of blood assays is a preferred method, in some embodiments, to render the extended, controlled-release formulation both effective and safe. Additionally, or alternatively, in some embodiments, the disclosed methods include the physician (or other medical professional) adjusting dosing as appropriate to provide the chosen range of nanomolar concentrations of phenserine and/or its metabolites in the brain, and in some embodiments, the adjustments are based on the results from assays of acetylcholinesterase activities in peripheral blood.

In some embodiments, methods for mitigating one or more pathologies following brain trauma or at least a portion of a cascade of pathologies associated therewith (e.g., preventing anecrotic cell death in neurons) includes maintaining therapeutic concentrations of the active compound with or without an anti-inflammatory drug until one or more presenting symptoms, impairments, testing results, analyses of bodily fluids, and/or other assessments conducted indicate that the neuropathological processes of degeneration following the brain trauma have resolved or the individual is no longer at risk of brain trauma. This may present as the individual stabilizing or returning to a pre-trauma state and may, in some embodiments, be determined through regular reassessments of the patient's functioning and symptoms and/or by similar assessments of cerebrospinal fluid or blood biological compounds reflecting or exerting pathological effects including but not limited to neuroinflammatory cytokines, markers of oxidative stress, IL-1$\beta$, IL-6, C-Reactive Protein, TNF-$\alpha$; failure of the blood-brain barrier, AP-1, AP-2; markers of astrocyte injury and death, S-100B; NSE, NAP-2, UCTH L-1 & L-2, A$\beta_{42}$, tau and p-tau, as measured directly in blood or CSF or in exosomes with brain marker labels, and comparing these to the values determined at baseline established when the patient presented for care.

In one embodiment, data from examinations are used to plot one or more pathological and/or clinical trends, to calculate standard errors of the mean or standard deviations, and to judge changes in any trend using the probability indicated by the statistic being used. In one embodiment, therapeutic doses of the disclosed extended, controlled-release composition will be continued so long as repeated assessments indicate continued improvements and can be terminated when scores from examination plateau. In some embodiments, the patient may deteriorate after cessation of treatment, wherein therapeutic doses of the disclosed extended, controlled-release composition may be resumed so long as discontinuation of treatment does not result in indications of active neuropathology. In some embodiments, if upon initial dosing the patient shows a stable performance over time, dosing will be continued so long as any clinical indications of active neuropathology are present and then discontinued using the trial off dosing and redosing as appropriate, as described above. In some embodiments, if upon initial dosing of the disclosed extended, controlled-release composition the patient's performance deteriorates without grounds for deterioration but due to previously unrecognized pathology or severity of the brain trauma, the patient will be maintained on therapeutic doses of the disclosed extended, controlled-release composition until measurements of his or her condition stabilize or improve. Additionally, or alternatively, further dosing adjustments may follow the above guidelines.

EXAMPLES

The following examples are illustrative and should not be interpreted as limiting the present disclosure. With respect to compounds used in any of Examples 1-14, phenserine ((−)-phenylcarbamoyleseroline) was synthesized in the form of its water-soluble tartrate salt (>99.9% chemical and 100% (−)-chiral purity). It should be appreciated that other phenserine salts may be used, including, for example, a salicylate salt, to provide combined anti-inflammatory activity. It should be appreciated that free base of the compound can appear to be ineffective because it is not adequately water soluble. In distinction to this error, a salt of phenserine should preferably be used to obtain solution of the compound and bioavailability where its lipophilic properties become advantageous, ensuring distribution and availability within the brain and its cells. In some embodiments, the free base can be advantageous, such as for use in transdermal and some other specialized means of phenserine administration.

The forthcoming examples show mitigation of one or more pathologies following brain trauma and/or mitigation of at least a portion of a cascade of pathologies associated therewith that are present in human and other mammalian brain traumas, including but not limited to neurodegenerations. For example, Example 1 demonstrates that phenserine exerts anti-inflammatory and other genetic and molecular effects in the brain of both mice and humans. Further, phenserine protects neurons in vitro against the otherwise toxic factors glutamate induced toxicity and oxidative stress (Example 2), which can be augmented with additive/synergistic combinations of anti-inflammatory drugs (Example 3). In in vitro and animal models phenserine protected neurons against anoxia and against concussive weight drop induced injuries (Examples 4 and 5). Since glutamate induced toxicity, oxidative stress, AP amyloid toxicity, and inflammation are each and severally present in brain traumas as well as particularly within neurodegenerations, including but not limited to Alzheimer's disease, Parkinson's disease, and so forth, these data support the use of phenserine to mitigate pathology following brain trauma (e.g., by providing protection to neurons from the hostile environments created by neuropathological cascades shared across neurodegenerations, and thereby protection from anecrotic cell death). It is widely accepted that neurons may prematurely and unnecessarily initiate anecrotic cell death processes such as apoptosis under hostile brain environmental conditions, which the neurons could otherwise survive.

Exemplary compositions of an extended, controlled-release medicament are provided (Example 6) followed by in vivo and in vitro testing of phenserine-based compounds, including examples of the pharmacokinetics and pharmacodynamics of phenserine-based compositions according to at least one embodiment of the present disclosure (Examples 7-10).

Thus, one surprising implication of this work is that the final debilitating and disease defining stage of the neuropathologies, the loss of neurons due to cell deaths and failed replacement, provides a distinct focus to drug interventions. In addition, the active compound of compositions disclosed herein and any effects expected or predicted from phenserine's specific countering of pathologies that precipitate neuronal death (or the cascade of events leading thereto), phenserine surprisingly provides a previously unidentified intervention with neurons preventing them from premature self-initiated anecrotic mediated cell death.

As provided in the forthcoming examples, the preservation of cells by compositions and methods described herein are evidenced in animals by preserved cognitive, behavioral, and other functions dependent on the integrity of neurons and the neuronal systems through which they function in the brain. Prevention of pathologies following brain trauma, including but not limited to neuronal losses from anecrotic cell death using compositions and methods disclosed herein will, in human neurodegenerative disorders leading to cognitive and/or functional impairments, mitigate or completely block the onset of these pathologies.

Example 1

Figure 1B:
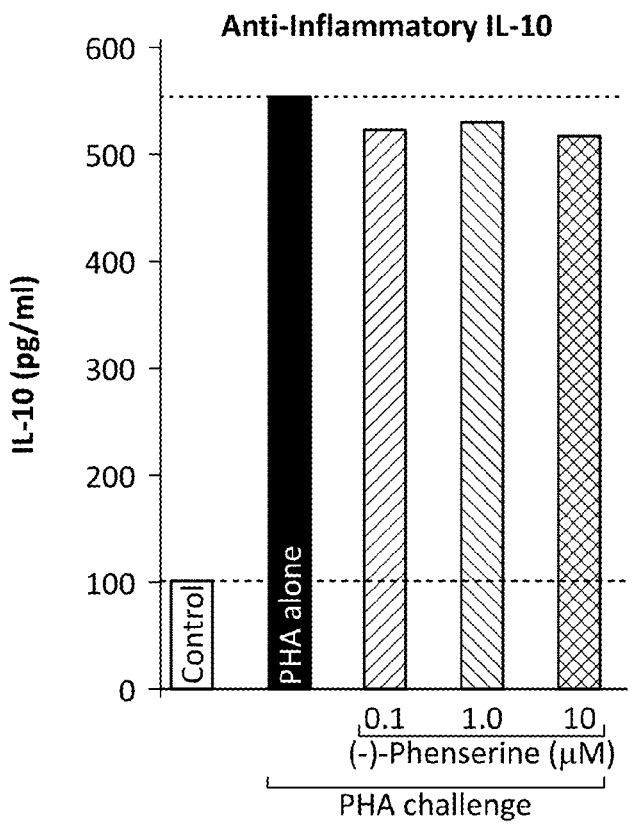

FIGS. 1A-1B provide support of the beneficial effects of phenserine on neurodegenerative pathologies important to brain traumas (e.g., traumatic brain injury, concussions, and sub-concussive injuries). Evidenced thereby is that the concentrations of phenserine and/or its metabolites (−)-N1, N8-bisnorphenylcarbamoyleseroline, (−)-N1-norphenylcarbamoyleserolined, and/or (−)-N8-norphenylcarbamoyleseroline exert anti-inflammatory and other genetic and molecular effects in the brain of both mice and humans. Briefly, human peripheral blood mononuclear cells (PBMCs) were isolated, from blood, then cultured and, in the presence and absence of phenserine for 24 h, challenged with phytohemagglutinin (PHA: 3 µg/mL; Sigma-Aldrich) to induce inflammation and cytokine production. The detection limit for these assays is <1 pg/mL for IL-1beta and <3 pg/mL for IL-10. The intra- and inter-assay CV was <10%. All results are expressed in picograms per milliliter. In these studies, phenserine (100 nM to 10 µM) substantially mitigated the phytohemagglutinin (PHA)-induced elevation in pro-inflammatory IL-1β (FIG. 1A) levels without impacting PHA-induced anti-inflammatory IL-10 levels (FIG. 1B). These data demonstrate benefits in four areas of neuropathology in addition to clinical benefits: inflammatory responses; oxidative stress responses; neuroprotection from anecrotic cell death and neuronal stem cell inhibition. Thus, in tissue culture of human inflammatory system cells, phenserine was shown to suppress the pro-inflammatory cytokine IL-1β (FIG. 1A) and to not suppress the anti-inflammatory cytokine IL-10 (FIG. 1B).

Example 2

Figure 2A:
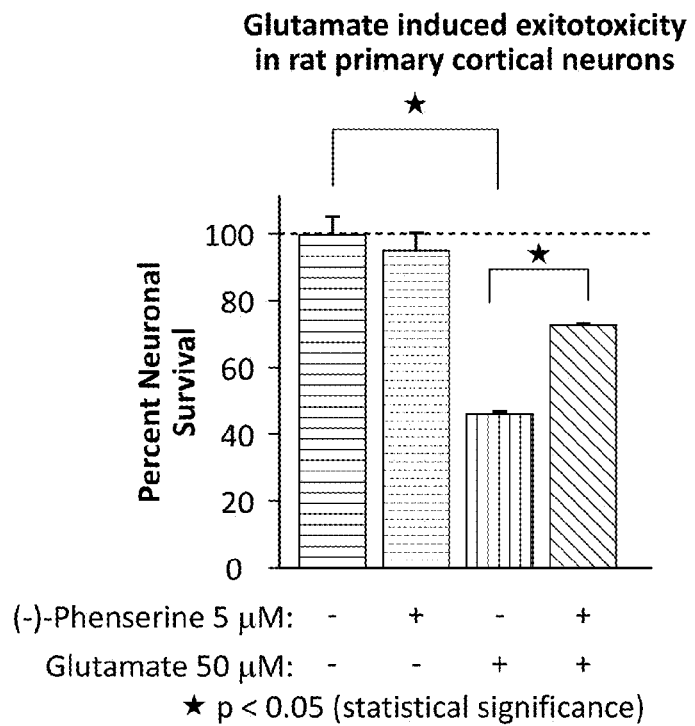
FIGS. 2A-2B illustrate increased neuronal survival in the presence of phenserine when challenged with glutamate induced excitotoxicity and oxidative stress, respectively.
Figure 2B:
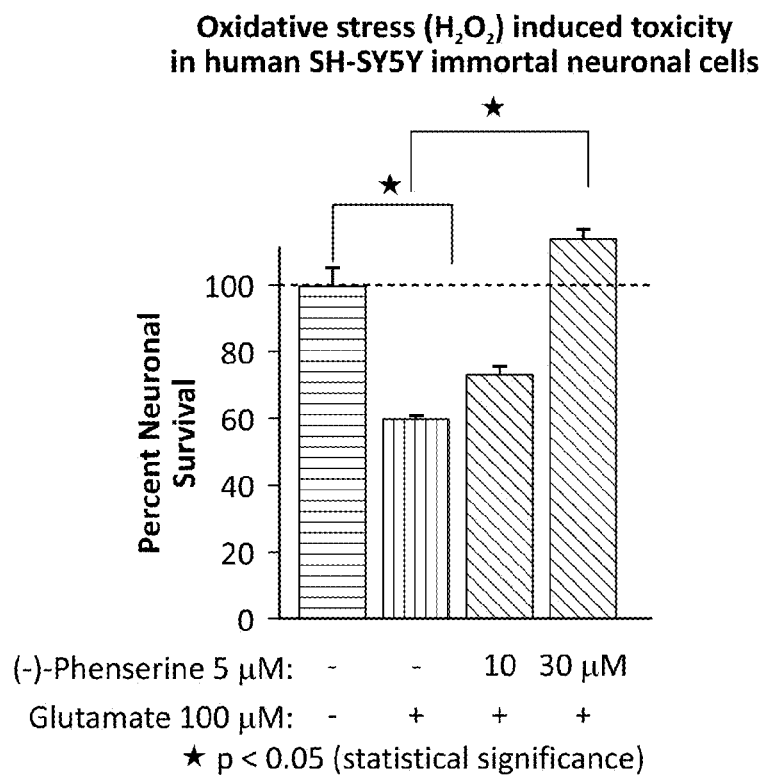

Referring now to FIGS. 2A-2B, illustrated are the effects of phenserine and on neuroprotection from anecrotic cell death, particularly with respect to glutamate-induced excitotoxicity and (FIG. 2A) and ($H_2O_2$)-induced oxidative stress (FIG. 2B)—two stresses known to be induced by TBI and other brain traumas—in cell culture models of rat primary cortical neurons and human immortal neuronal cell line SH-SY5Y, respectively.

Briefly, cultured hippocampal neurons in triplicate were prepared from 18-20 day rat (Sprague Dawley) embryos and were cultured for 7 days. They were treated with phenserine (5 µM) followed by the addition of an excitotoxic concentration of glutamate (50 µM). Neuronal viability was assessed 24 h after addition of glutamate. The results are plotted as percent neuronal survival ±SEM. As shown in FIG. 2A, glutamate significantly reduced cell viability by 53.5%, which was mitigated by phenserine by a return to 73.5% of control levels. Human SH-SY5Y cells were plated and after 24 h, cells were exposed to phenserine, (10 and 30 µM) followed by oxidative stress, induced by 100 µM $H_2O_2$. Twenty-four hours later cell viability was quantified. As shown in FIG. 2B, phenserine treatment significantly ameliorated the $H_2O_2$-mediated neuronal toxicity.

As is known, drug concentrations for pharmacological effects in human immortal neuronal cell line SH-SY5Y cell cultures are consistently higher than those in primary (not immortal) cell lines or in other in vitro experiments. Therefore, these results are not inconsistent with dosing effectiveness in vivo at tissue nanomolar concentrations.

Example 3

The combination of phenserine with the anti-inflammatory drug aspirin exerts a synergistic neuroprotective effect against $H_2O_2$-induced oxidative stress in human SH-SY5 neuronal cells (FIG. 3). The combination of phenserine with the anti-inflammatory drug naproxen exerts additive and/or synergistic neuroprotective and neurotrophic effects in human SH-SY5 neuronal cells (FIGS. 3B-3D).

Human SH-SY5Y neuronal cells were seeded in 96-well plates at a density of 1×10⁵ cells per well and allowed to grow for 24 h. Cells were then treated with various concentrations of non-steroidal anti-inflammatory drugs, as illustrated with aspirin (ASA) ($10^{-5}$ M) or phenserine (Phen) ($10^{-7}$ M, $10^{-6}$ M) or combinations ASA and Phen for 2 h in low serum (0.5% serum) media. Thereafter, cells were challenged to oxidative stress by $H_2O_2$ addition to half of the wells at a final concentration of 50 µM. At 18 h thereafter a MTS assay was performed per the manufacturers protocol (Abcam, Cambridge, Mass.) to measure cell viability.

Figure 3A:
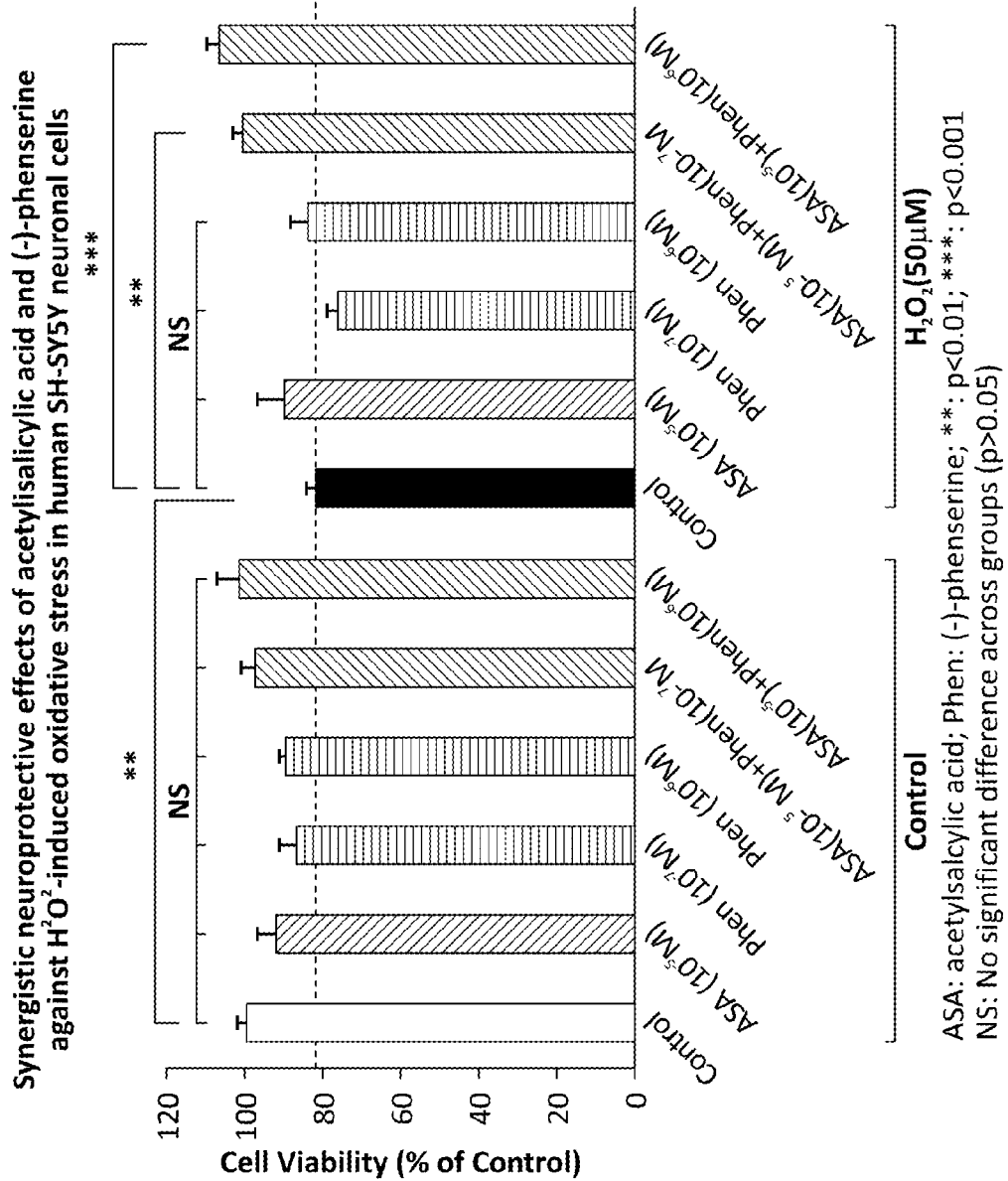
FIGS. 3A-3D illustrate additive and/or synergistic effects of anti-inflammatory drugs and phenserine against oxidative stress in neuronal cells.
Figure 3B:
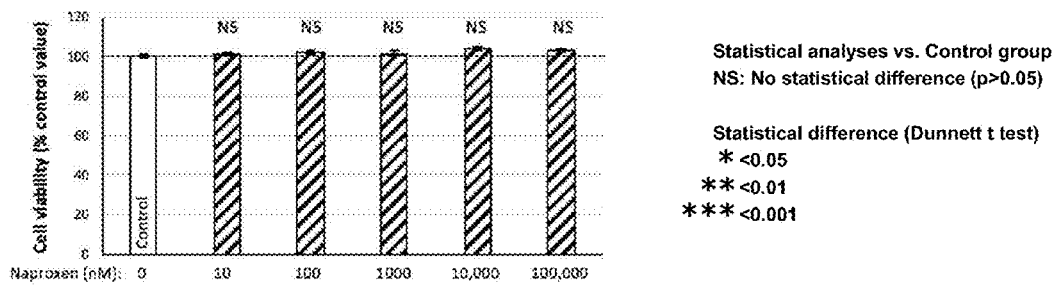

As demonstrated in FIG. 3A, where ASA ($10^{-5}$ M) or (−)-Phen ($10^{-7}$M, $10^{-6}$ M) alone demonstrated no activity (these were selected doses that were sub-therapeutic and thus possessed no neuroprotective actions), the combination of these two sub-therapeutic doses (i.e., ASA ($10^{-5}$ M)+(−)-Phen ($10^{-7}$ M, $10^{-6}$ M)) fully mitigated oxidative stress-induced cellular death. Data are presented as mean±S.E.M., n>3 per group and p-values of <0.05 were considered significant.

Figure 3C:
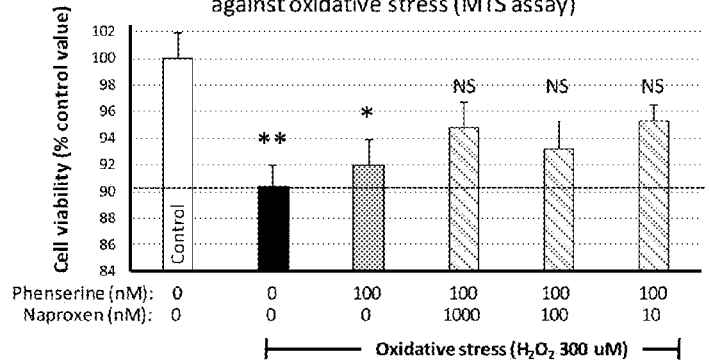

In addition to aspirin, other anti-inflammatory drugs act synergistically with phenserine to provide neuroprotective effects. For example, instead of aspirin (as shown in FIG. 3A), an NSAID, naproxen, was used under the same experimental conditions at concentrations in FIGS. 3B-3D. As demonstrated in FIG. 3B, naproxen is well tolerated by SH-SY5Y neuronal cells at concentrations between 10 nM to 100,000 nM but does not show activity in relation to trophic actions. FIG. 3C illustrates that following oxidative stress ($H_2O_2$ at 300 µM) there is a statistically significant loss in cell viability (at least 10% cellular vs. unchallenged control). Addition of a low dose of phenserine alone (100 nM) does not statistically mitigate this loss (as evaluated versus the control group). However, the addition of the same concentration of phenserine (100 nM) in combination with naproxen (10 to 1000 nM) results in neuronal survival that is not statistically different from control values, indicating a neuroprotective effect of the combined treatment of phenserine and naproxen.

Figure 3D:
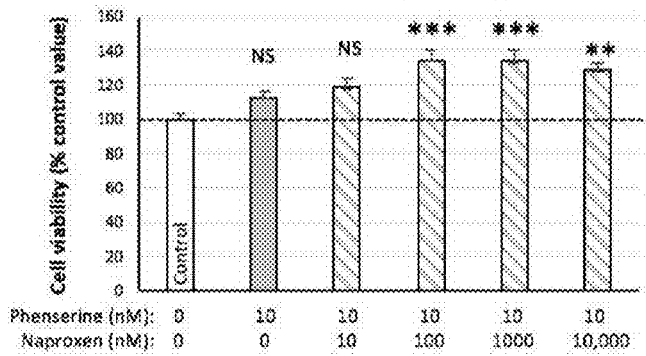

FIG. 3D illustrates that the combination of a low dose of phenserine (10 nM) that additionally has no neurotrophic action, with naproxen (100 nM) results in a statistically significant neurotrophic effect (elevating cell survival to about 135% of the control values).

Example 4

Figure 4:
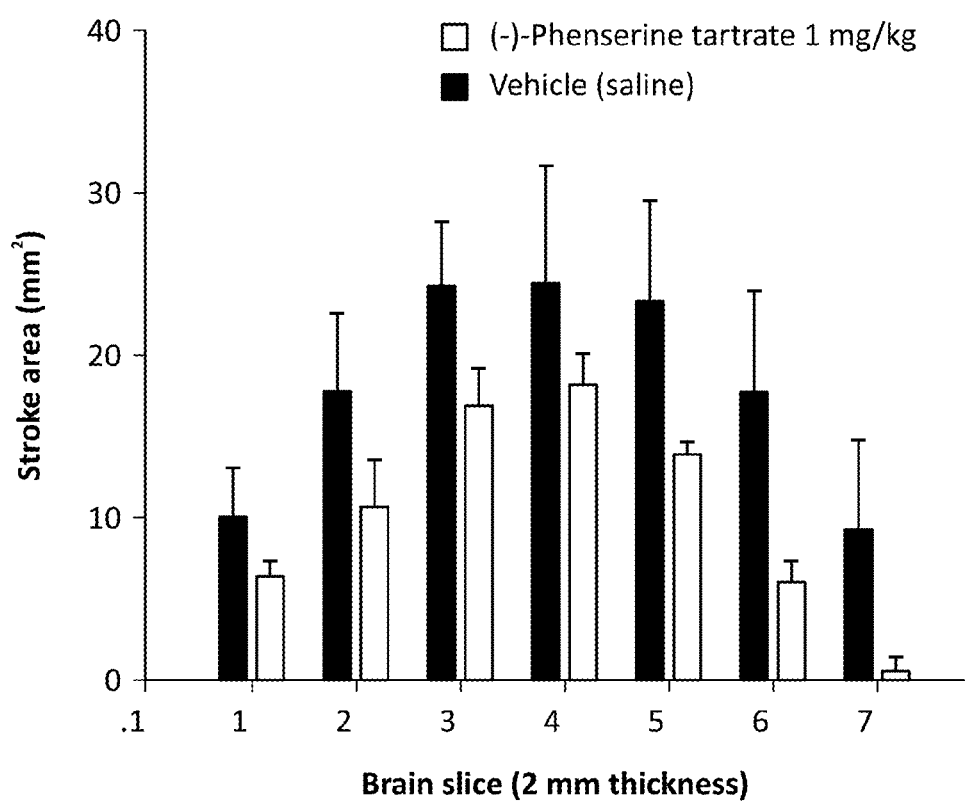
FIG. 4 illustrates neuro-protective effects of phenserine in an in vivo model of brain ischemia.

The data in FIGS. 4, 5A, and 6A-6B support phenserine providing neuroprotective effects by both modifying concentrations of biochemical factors in ways consistent with amelioration of the disease process, reduction of cognitive and functional clinical impairments in patients, and reduction of risk of chronically active neuropathologies precipitated by a concussion or TBI, and by directly reducing neurons' activation of anecrotic cell death processes in the presence of pathological factors in the neuron itself or in the neuronal environment. That is to say, phenserine treatment results in reductions of neuronal conditions favorable to the induction of anecrotic cell death and increased resistance of the neuron to self-inducing anecrotic cell death. Briefly, FIG. 4 illustrates post-treatment of induced brain ischemia with phenserine reduced brain infarction area in rats. Adult male Sprague-Dawley rats (250 to 350 g weight) were anesthetized with chloral hydrate (0.4 g/kg, intraperitoneally) and right middle cerebral artery (MCA) was ligated and the common carotids were clamped bilaterally using nontraumatic arterial clips to induce focal infarction in the cerebral cortex on day 0. The ligature and clips were then removed after 60 minutes of ischemia to allow repercussion and to generate an infarction limited to the right cerebral cortex. The core body temperature of animals was maintained at 37° C. throughout the procedure. Animals were randomly separated into two similar groups, and treated with either phenserine (1 mg/kg/day), or vehicle (physiological saline) daily starting at 1 day post-MCA occlusion and continuing to day 4 post stroke. Animals were euthanized and the brain removed on day 5 post stroke. The brain was then sliced into 2 mm thick sections, which were incubated in a 2% triphenyltetrazolium chloride (TTC) solution (Sigma, St. Louis) for 15 min at room temperature and then were transferred into a 4% paraformaldehyde solution for fixation. The area of infarction within each slice was measured using a digital scanner and the Imagetools program (University of Texas Health Sciences Center, San Antonio, Tex.). A volume of infarction was obtained from the product of the average slice thickness (2 mm) and sum of infarction areas in all brain slices examined. The infarction area was significantly reduced in rats treated with phenserine (p=0.001), as compared to vehicle (two way ANOVA+Newman-Keuls test). Data are presented as mean±S.E.M., n=8 rats per group and p-values of <0.05 were considered significant.

Figure 5A:
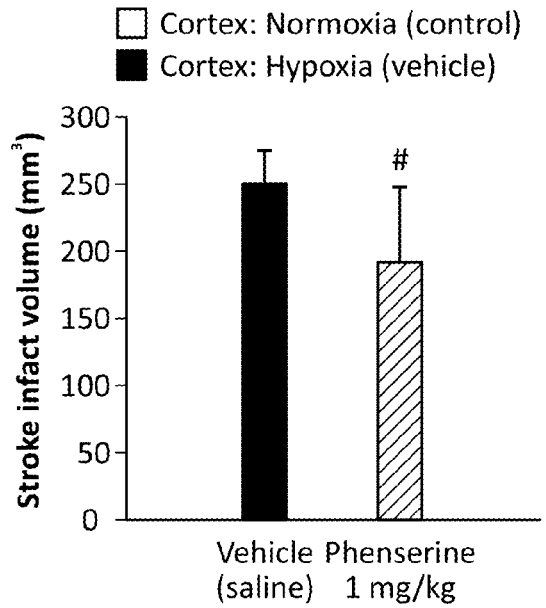
FIGS. 5A-5C illustrate neuro-protective effects of phenserine in an in vivo model of brain ischemia.
Figure 5B:
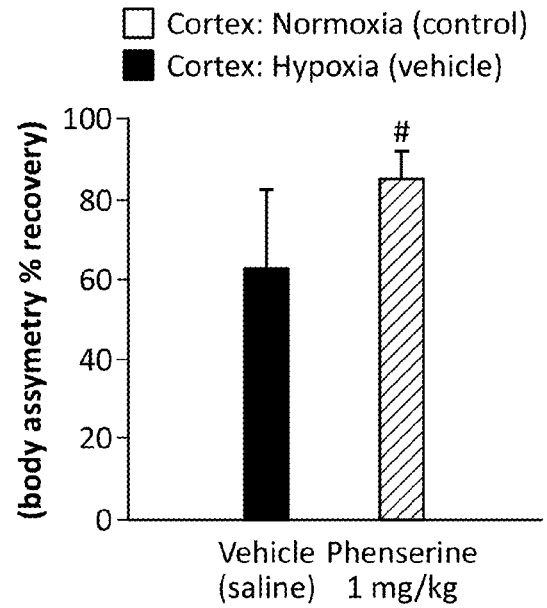
Figure 5C:
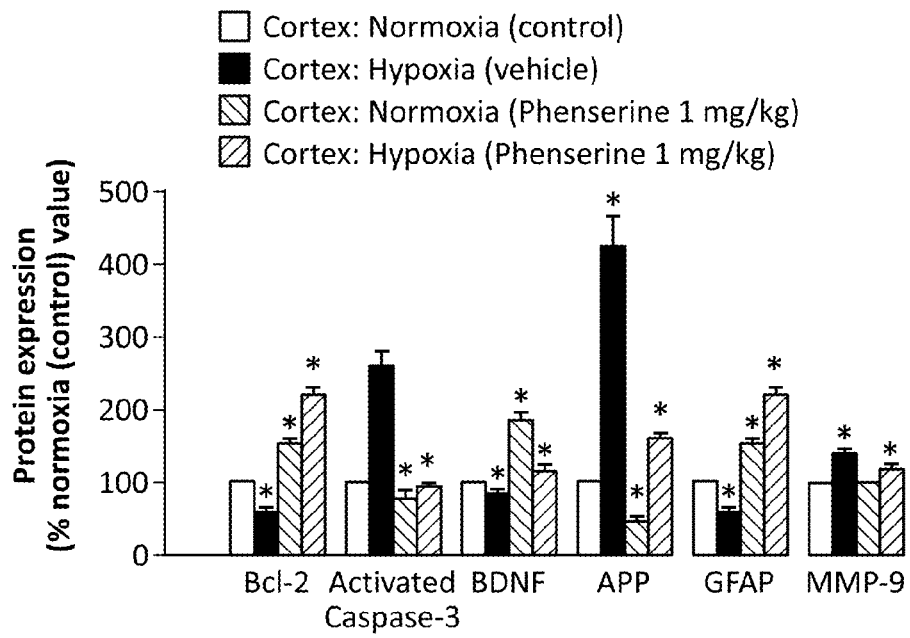
Figure 6A:
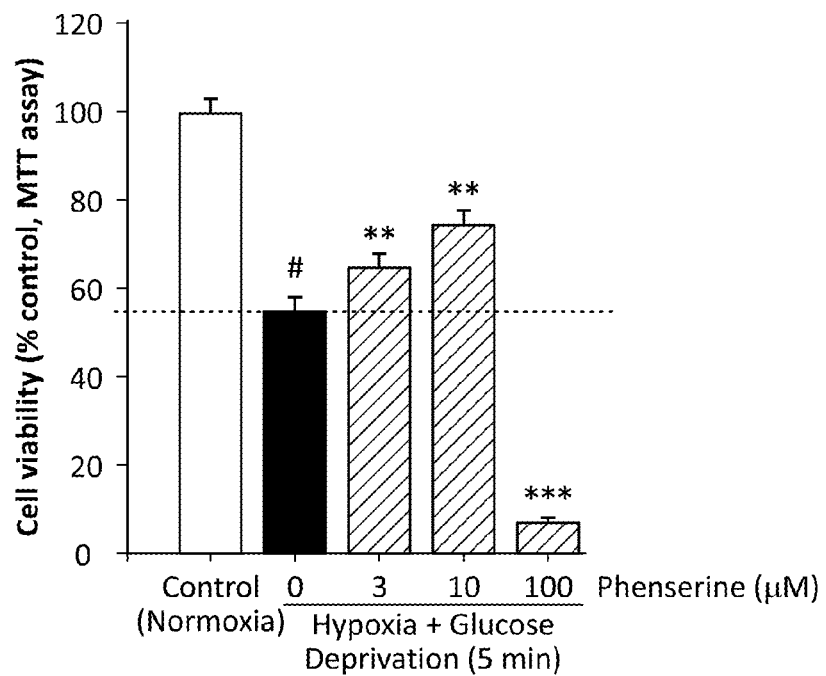
FIGS. 6A-6B illustrate neuro-protective effects of phenserine in an in vitro cell culture model.
Figure 6B:
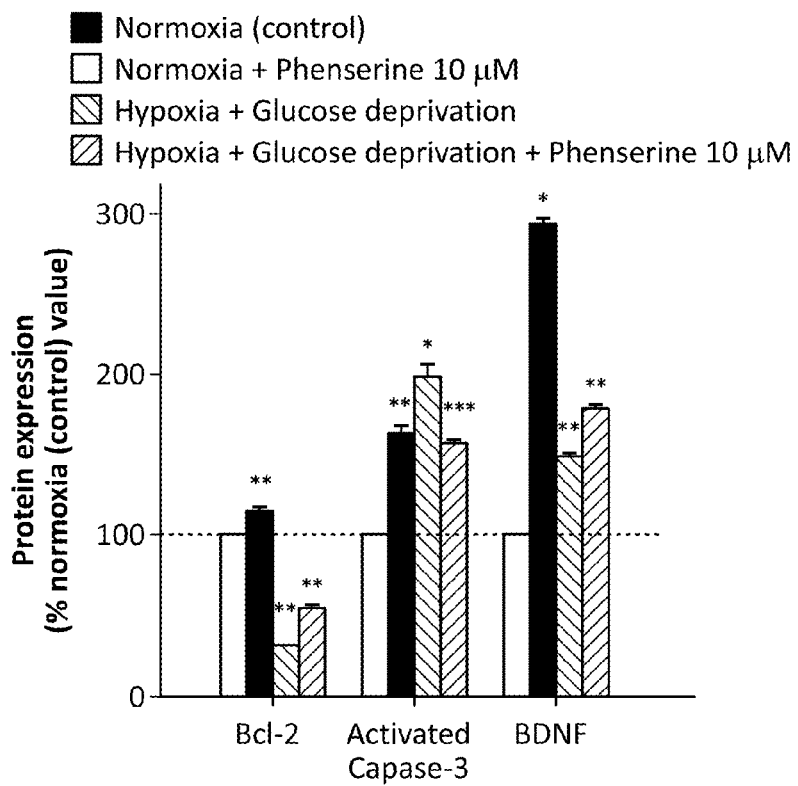

FIGS. 5A-5C and 6A-6B illustrate effects of phenserine in the rodent focal cerebral ischemia model in vivo (FIGS. 5A-5C) and oxygen-glucose deprivation/reperfusion (OGD/RP) damage on SH-SY5Y cells in vivo (FIGS. 6A-6B). Briefly, Human neuroblastoma SH-SY5Y cells were incubated in oxygen-glucose deprivation and hypoxia using serum- and glucose-free media and 95% $N_2$ and 5% $CO_2$ for 5 minutes. Adult male Sprague-Dawley rats (250 to 350 g weight) were anesthetized with chloral hydrate (0.4 g/kg, intraperitoneally) and right middle cerebral artery (MCA) was ligated for 60 minutes. The core body temperature of animals was maintained at 37° C. throughout the procedure. Animals were randomly separated into two similar groups, and treated with either phenserine at the various concentrations, or vehicle (physiological saline) twice daily prior to the MCA occlusion.

Pre-treatment of induced brain ischemia with phenserine reduced brain infarction area (FIG. 5A), cell death, improved body symmetry (FIG. 5B), increased brain-derived neurotrophic factor (BDNF) and B-cell lymphoma 2 (Bcl-2; an anti-apoptotic protein associated with cell survival) expression, but decreased, in brain and SH-SY5Y cells, activated-caspase 3 levels (a pro-apoptotic protein associated with cell death), amyloid precursor protein (APP; an acute phase neuronal protein associated with Alzheimer's disease) and glial fibrillary acidic protein (GFAP) expression (a marker of activated astrocytes) in rats (FIG. 5C). Phenserine also reduced matrix metallopeptidase 9 (MMP-9) in SH-SY5Y cells (FIG. 5C). MMP-9 is involved in the degradation of the extracellular matrix that supports neuronal viability and acts on pro-inflammatory cytokines, chemokines and other proteins to regulate inflammation. The concentration changes associated with phenserine for each of these biochemical compounds reduces the risk of anecrotic cell death for neurons.

Pre-treatment of induced brain ischemia with phenserine reduced brain infarction area (FIG. 5A), cell death, improved body symmetry (FIG. 5B), increased expression of brain-derived neurotrophic factor (BDNF) and B-cell lymphoma 2 (Bcl-2; an anti-apoptotic protein associated with cell survival), but decreased levels of activated-caspase 3 (a pro-apoptotic protein associated with cell death) levels and expression of amyloid precursor protein (APP; an acute phase neuronal protein associated with Alzheimer's disease) and glial fibrillary acidic protein (GFAP) in brain and SH-SY5U cells in rats (FIG. 5C). Phenserine also reduced matrix metallopeptidase 9 (MMP-9) in SH-SY5Y cells (FIG. 5C). MMP-9 is involved in the degradation of the extracellular matrix that supports neuronal viability and acts on pro-inflammatory cytokines, chemokines and other proteins to regulate inflammation. The concentration changes associated with phenserine for each of these biochemical compounds reduces the risk of anecrotic cell death for neurons.

Example 5

Figure 7A:
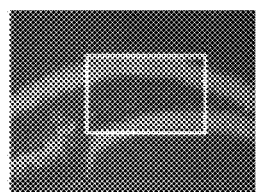
FIGS. 7A-7C illustrates a mouse model of degenerating neurons following mild traumatic brain injury.
Figure 7B:
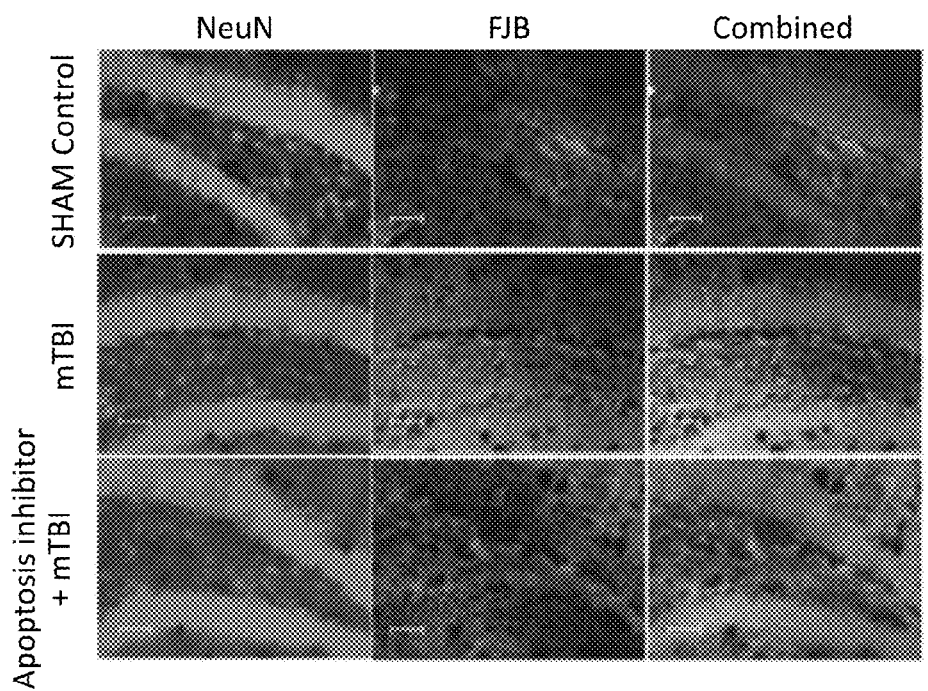
Figure 7C:
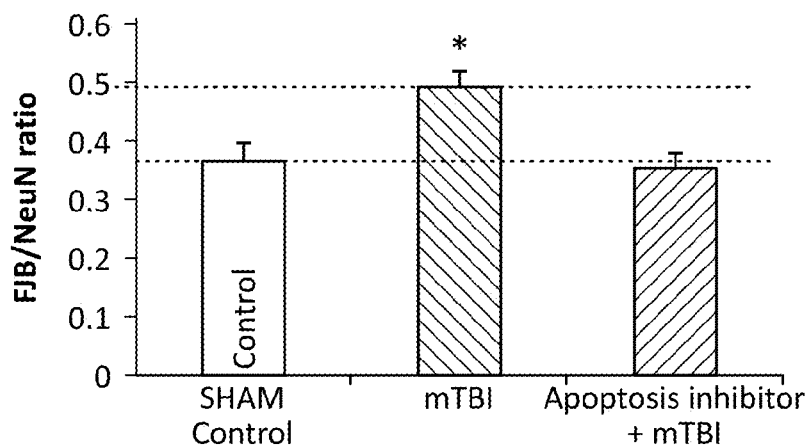

Mild TBI was demonstrated to induce diffuse neuronal apoptotic loss within the dentate gyrus of the hippocampus in an animal model (FIGS. 7A-7C). To evaluate neuron viability and TBI-induced apoptosis, mice subjected to a 30 g weight drop TBI [with or without treatment with a well-characterized pharmacological tool to inhibit apoptotic cell death, specifically the p53 inactivator PFT-α (2-imino-2,3,4,5,6,7-hexahydrobenzothiazole) following concussive injury] or sham procedure (healthy controls) were killed at 72 h, the brains were removed, and immunohistochemistry was undertaken to evaluate degenerating neuronal cells within the dentate gyrus of the hippocampus. Brain sections were stained for NeuN (a marker of mature neurons) and Fluoro-Jade B (FJB: a marker of degenerating neurons), which allowed analysis of neurons undergoing apoptotic neurodegeneration. In this manner, a ratio of the numbers of degenerating neurons over the number of mature neurons was used as an index of trauma-induced cellular health. Prior to removal of their brain, mice were anaesthetized with a combination of ketamine (100 mg/kg) and xylazine (10 mg/kg) and were perfused transcardially with 10 mL of phosphate buffered saline followed by perfusion with 20 mL of a 4% paraformaldehyde (PFA) buffer. The brains were removed and then post-fixed overnight in the same fixative solution and then transferred to 1% PFA. Thereafter, the brains were submerged in a 30% sucrose solution for 48 h prior to sectioning.

For sectioning, thirty micrometer (30 μM) thick free floating coronal sections were prepared on a cryostat. These sections were collected in a cryoprotectant solution containing phosphate buffer, ethylene glycol, and glycerin, and stored at −20° C. Every twelfth section throughout the brain was stained with a mouse primary antibody that detects NeuN (Millipore; MAB377, diluted 1:50 in incubation buffer), after the incubation with primary antibody the sections were washed and then incubated with a Cy3 labeled anti-mouse secondary antibody (Jackson; 715-165-150, diluted 1:300 in incubation buffer). Probed sections were mounted onto 2% gelatin coated slides and stained with FJB (Millipore; AG310). The slides were evaluated under a Zeiss Axiovert 200 fluorescence microscope (Zeiss) with cell counts across identical fields.

Illustrated in FIG. 7A, the field within the box represents the hilus of the dentate gyrus within the hippocampus of a mouse. This boxed region is shown at a higher magnification in FIG. 7B (scale bar=100 μm) with selected immunohistochemical staining for NeuN or FJB; a combined NeuN, FJB overlay is shown in the final column of images in FIG. 7B. The quantification of neuronal degeneration within the dentate gyrus is illustrated as a ratio of the number of neurons positively stained with FJB (degenerating neurons) divided by neurons positively stained with anti-NeuN in sham control, mTBI, and mTBI with administration of an apoptosis inhibitor groups of animals (see FIG. 7C; (*$p<0.01$; Bonferroni post hoc [$F(2,19)=9.219$, $p=0.002$]; values are mean±SEM, of n=6-10 mouse brains.).

As illustrated in FIG. 7B and quantified in FIG. 7C, there is neuronal loss in the brain following a concussive head injury (mTBI), where both necrotic and anecrotic (e.g., apoptotic) neuronal death occur. Use of the anti-apoptotic pharmacological tool PFT-α shortly following concussive injury mitigated anecrotic (apoptotic) cell death (as evaluated at 72 hours—a time of significant anecrotic cell death), and animals treated with PFT-α were spared from cognitive impairments (as evaluated at 7 and 30 days after injury) (data not shown).

Phenserine was shown to affect key proteins and cascades involved in mitigating anecrotic cell death (see, for example, FIG. 5C where phenserine treatment significantly increased anti-apoptotic protein Bcl-2 and concomitantly significantly decreased pro-apoptotic activated caspase-3) and elevate key trophic/neuroprotective proteins both in vivo and in cellular studies to inhibit anecrotic cell death (see, for example, elevated BDNF levels in FIGS. 5C and 6B). These effects translate into improved brain pathological outcomes, and as described below, these effects additionally provide improved behavioral outcomes.

The same model of concussive head injury described above with respect to FIG. 7 was used in the experiments described below with respect to FIGS. 8 and 9. We evaluated the clinical-behavioral actions of phenserine in the aforementioned simulated mTBI mouse model following two doses (2.5 and 5.0 mg/kg, i.p., BID×5 days) initiated 30 min following injury. Whereas phenserine has reported anticholinesterase activity with a selectivity for acetyl- vs. butyryl-cholinesterase, studies in mice demonstrate no inhibition of either enzyme 24 hours following the final dose. Previous studies of drug and metabolite concentrations have shown acetylcholinesterase inhibition to be present when any concentration of drug or metabolite have been detected. In this study dosing of mice continued through day 5 post injury, initiation of behavioral evaluation began on day 7, and this testing began 48 hours after the last dose of phenserine or well past the period of time where the drug has been shown to have any pharmacological activity or presence. This indicates that the significant amelioration of induced memory deficits with phenserine treatment (FIGS. 8 and 9) are not cholinergically induced via direct cholinesterase inhibitory action on behavior or by other direct effects from the drug being present in brain and present at a target site since acetyl- and butyrylcholinesterase activities by day 7 are no longer inhibited by phenserine or its metabolites indicating absence of drug from brain targets. Drug and its metabolites have been shown undetectable when no anti-cholinesterase activities are present.

Behavioral evaluation of animals subjected to injury in the model was undertaken at 7 days and later after injury, in accord with previous time-dependent studies. The assessed behavior involved (i) recognition memory assessed by the classical novel object recognition paradigm (FIG. 8) and, (ii), spatial memory evaluated by the Y-maze paradigm (FIG. 9), which in prior studies we and others found impaired by the induced injury. The former task refers to the ability to discriminate a previously encountered (familiar) item from a novel one; a task that has become a valuable tool in basic and preclinical research for investigating the neural basis of memory, and that has parallels to visual paired-comparison tasks in studies in humans and monkeys. Damage to the hippocampus is sufficient to produce impaired recognition memory. The latter task, spontaneous spatial memory in the Y-maze, is likewise considered a hippocampal-dependent test and, importantly, both recognition and spatial memory are impaired in humans with traumatic brain injury and concussions. The hippocampus, in particular, appears to be particularly vulnerable to injury-induced anecrotic neuronal death.

We confirmed the presence of neuronal and other brain cell injuries and death following the methods for producing brain injury and assessing drug effects on said injuries in mice (see FIGS. 7A-7C). Using tissue from the brains of these behaviorally evaluated animals, by study of gene expression relevant to neuronal cell death, we determined that the phenserine behavioral effects (FIGS. 8 and 9) reflect drug induced ameliorations of neuropathologies following the brain injury (see for example FIGS. 1-3).

Figure 8:
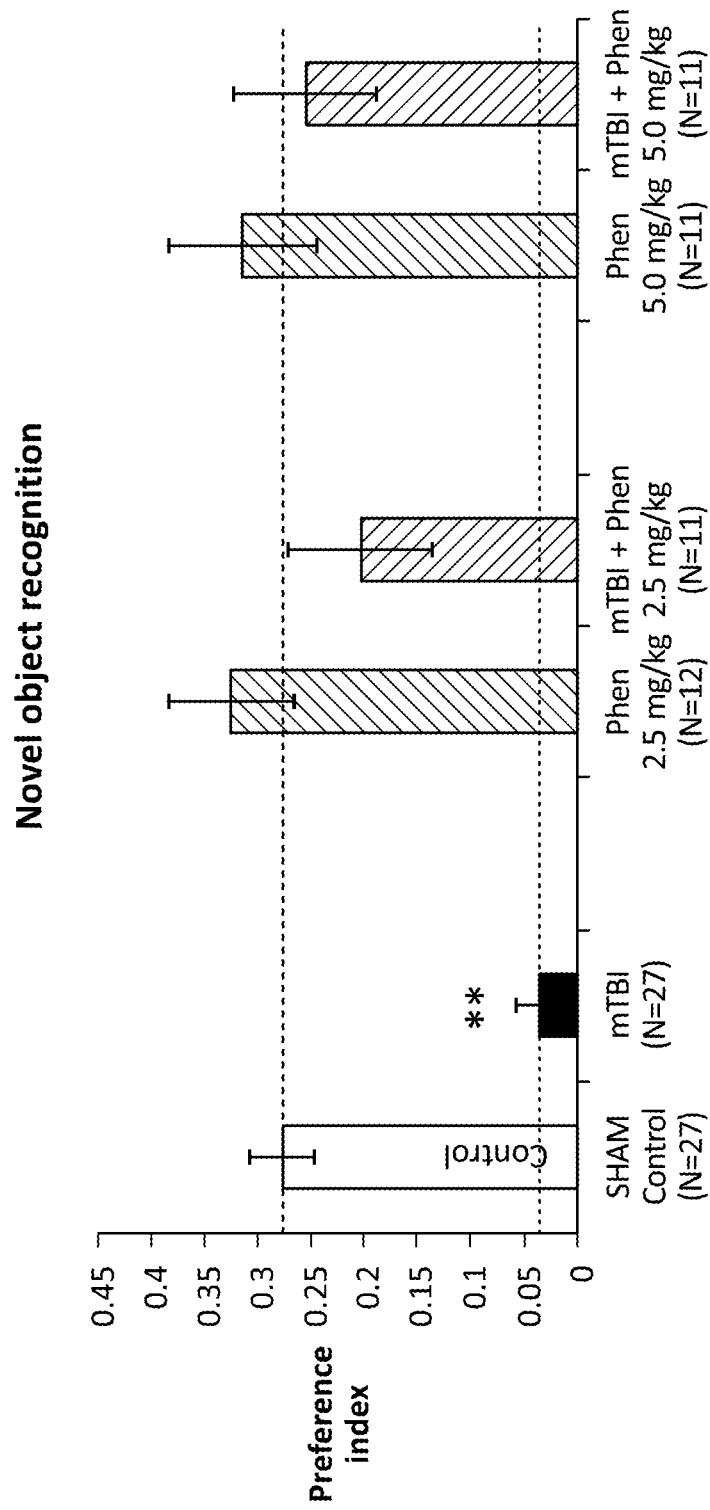
FIG. 8 illustrates results of novel object recognition in mice following mild traumatic brain injury and phenserine treatment.

As shown in FIG. 8, the novel object recognition test was used to evaluate visual recognition memory and was performed 7 days and later after head injury. Amelioration of spatial and visual memory impairments in a close head, mouse model of mild TBI (mTBI) was assessed using Novel Object Recognition that was performed two days and later following cessation of clinically translatable dosing of phenserine (2.5 and 5.0 mg/kg BID×5 days initiated post mTBI). These results occurred in the absence of anticholinesterase activity, a marker of the presence of phenserine and/or its (−)-N1, N8-bisnorphenylcarbamoyleseroline metabolite. The rapid metabolic degradation of these compounds ensures that no pharmacological concentrations are evident in the brain during the cognitive evaluations performed 2 days and later.

The mTBI mice demonstrate a deficit in visual memory compared with control uninjured (Sham) animals ($p<0.01$). Phenserine administration significantly ameliorated this damage (in both doses $p<0.01$). One-way ANOVA revealed a significant effect between groups [$F(5, 98)=7.770$, $p=0.000$]. Fisher's LSD post hoc analysis revealed that the preference index of the "mTBI" group was significantly lower than all other groups (**$p<0.01$).

Figure 9:
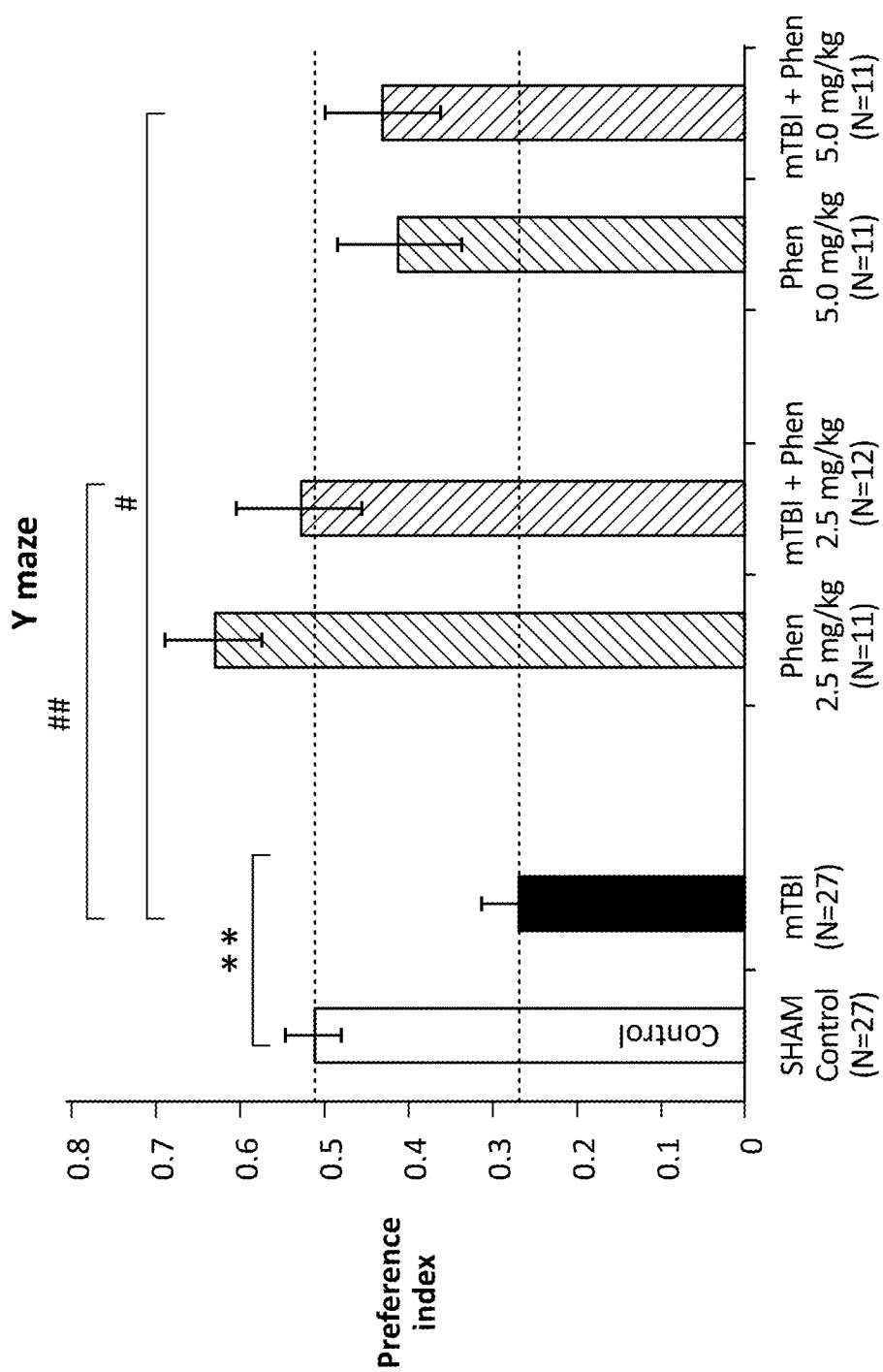
FIG. 9 illustrates results of a Y-maze cognitive test in mice following mild traumatic brain injury and phenserine treatment.

The Y maze test was used to evaluate spatial memory and was performed 7 days and later after head injury (FIG. 9). Amelioration of spatial and visual memory impairments in a close head, mouse model of mTBI was assessed using Y Maze two days and later following cessation of clinically translatable dosing of phenserine (2.5 and 5.0 mg/kg BID×5 days) initiated post mTBI. These results occurred in the absence of anticholinesterase activity, a marker of the presence of phenserine and/or its (−)-N1, N8-bisnorphenylcarbamoyleseroline metabolite. The rapid metabolic degradation of these compounds ensures that no pharmacological concentrations are evident in the brain during the cognitive evaluations performed 2 days and later.

The mTBI mice demonstrate a significant deficit in spatial memory compared with control uninjured (Sham) animals (**$p<0.01$). Phenserine administration significantly ameliorated this damage (##$p<0.01$ for 2.5 mg/kg and (#$p<0.05$ for 5 mg/kg). One-way ANOVA revealed a significant effect between groups [$F(5,105)=6.190$, $p=0.000$]. Fisher's LSD post hoc analysis revealed that the preference index of the "mTBI" group was significantly lower than all other groups other than "Phenserine only (Phen)" 5 mg/kg (*$p<0.05$, **$p<0.01$).

Example 6

Figure 10:
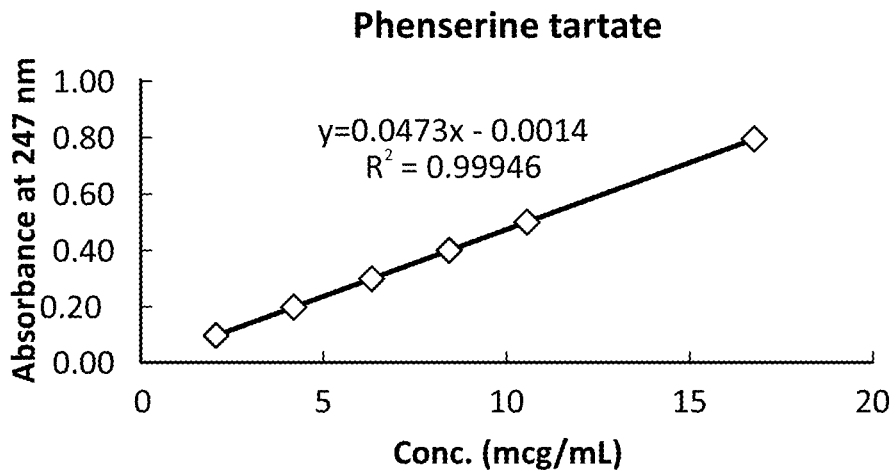
FIG. 10 illustrates a UV standard curve for an extended controlled-release phenserine combination tablet.

The following approaches were used to develop an exemplary extended controlled-release tablets (ECRT). In an initial study testing for release from a ECRT formulation phenserine tartrate was mixed with Polyox™, WSR 303 LEO NF, Dow chemical, VBN #WI2455SR3 and HPC, high grade, Nippon Soda ltd., Lot #NIE-3401 using 40 mg of drug and 280 mg of polymer (1:7 drug:polymer ratio). Mixed well with spatula following geometric dilution the powders were compressed in a die (0.5 inch) under a Carver press at 3000 pounds of pressure for 30 seconds. The Release Dissolution Test (n=2) was conducted, consistent with CGMP, using a USP dissolution paddle apparatus (VK700) operating at 37° C. and a rotating speed of 100 rpm. Distilled water (900 mL) was used as the dissolution medium. At each time point, 5 mL of dissolution sample was taken and monitored with UV spectrometry (HP 8453) at 247 nm. After obtaining a satisfactory UV standard curve, (FIG. 10), 24 release results were determined for HPC and Polypox (100% and 9%) and hourly (10 min-10%; 1 hr. 58%; 2 hr. 85%)

The drug release was almost completed in four hours (around 90%). In a following experiment phenserine tartrate (1.3 g) and HPC polymer (9.1 g, 1:7 drug:polymer ratio) were mixed well with the same methods to produce 32 tablets, weights ranging from 233 mg to 247 mg with a thickness ~⅛ inch (~0.32 cm). After satisfactory UV spectrometry (HP 8453) at 247 nm to determine the phenserine content in three samples of the mixed powder (~90-100 mg) in 250 mL each of distilled water, a detected average percent (93.9%) drug content indicated 28.2 mg rather than the target amount of 30 mg. Then phenserine (0.25 g) and HPC polymer (1.75 g, 1:7 drug:polymer ratio), using the above methods, were used to produce tablets weighing from 243 mg to 248 mg with a thickness ~⅛ inch (or ~0.32 cm). Dissolution testing then used simulated gastric fluid (SGF) without pepsin, prepared as described in the United States Pharmacopeia (USP 26) with distilled and deionized water, concentrated HCl (7 mL) to ~900 mL of water and NaCl (2 g) brought to 1 L with a pH=1.12 and simulated intestinal fluid (SIF) without pancreatin, prepared as described in the United States Pharmacopeia (USP 26), with KH2PO4 (6.8 g) and NaOH (0.89 g) dissolved in ~900 mL of water, brought to 1 L with pH=6.73. The Release dissolution tests (n=3) were conducted according to the methods and UV calibration described above for phenserine tartrate in SGF and SIF separately. Drug release after 48 hours were HPC 96% and 72% respectively for these GI modeled conditions or 33% and 35% at 6 hours, slightly slower compared to release in water.

Figure 11:
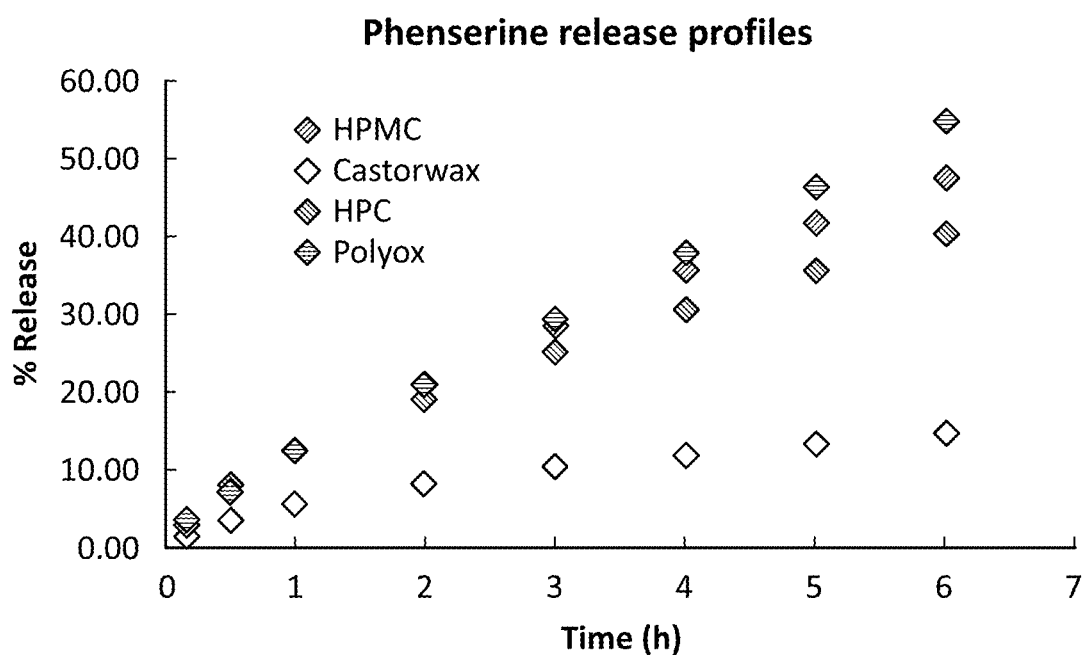
FIG. 11 illustrates dissolution release testing of various wax and/or hydrophilic polymer formulations for use as an extended controlled-release formulation.

In a subsequent formulation phenserine tartrate with Polyoxyethylene, NF (Polyox™, WSR 303 LEO), Colorcon, VBN #WI2455SR3, Hydroxypropylcellulose (HPC, high grade), Nippon Soda ltd., Lot #NIE-3401, Hydroxypropyl methylcellulose (HPMC), K15M, Dow Chemical, Lot # MM92031412K, and Hydrogenated castor oil, NF (Castorwax®), Caschem, Lot #00121431 were compared. For the wax (~420 mg) was melted at ~70-80° C. and then mixed with powdered phenserine (~60 mg) using a spatula to get a 1:7 drug:wax ratio. The cooled and congealed wax/phenserine mixture was ground to a powder. For all other formulations, ~40 mg of phenserine and 280 mg of polymer (1:7 drug:polymer ratio) were mixed well as powders. The above methods were then applied. In Dissolution Release testing HPMC, Castorwax, HPC, and Polyox averaged 48%, 15%, 40%, and 54% release at 6 hours (FIG. 11).

In summary, these results show that the release of phenserine can be controlled using a wax formulation or hydrophilic polymer formulations and therefore exemplify how formulations which use acceptable excipients for a pharmaceutical tablet can be employed to control the release of phenserine in the gastrointestinal track. By varying the excipients, we are able to control the duration of phenserine release, and by varying the concentrations of phenserine in each ECRT mix of excipients, we are able to vary the hourly release amounts of drug. Using these data, we developed an ECRT that provided phenserine over 24 hours, as shown in vitro and in vivo (Examples 7-11 corresponding to FIGS. 12-16).

Example 7

Figure 12A:
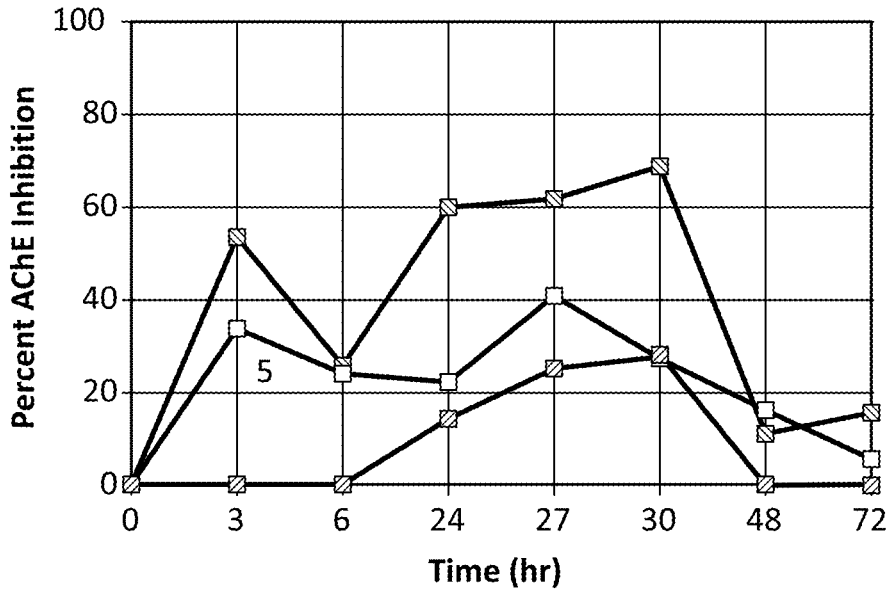
FIGS. 12A-12B illustrate in vivo acetylcholinesterase inhibition following administration of a slow release formulation containing phenserine.
Figure 12B:
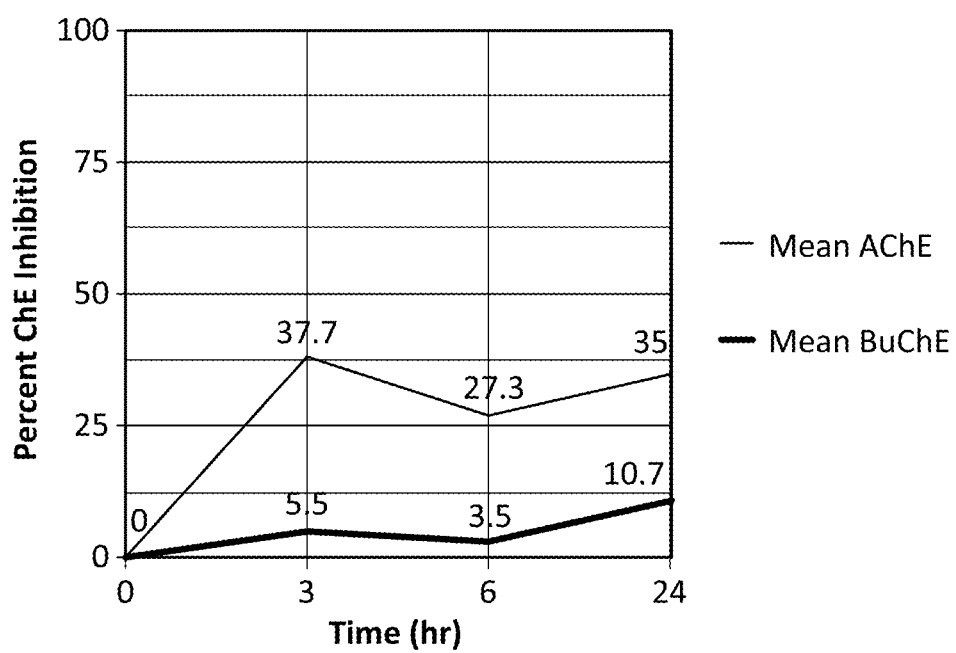

Initially a single sustained release oral formulation of phenserine was administered to three separate dogs, which resulted in sustained inhibition but also substantial variability among individuals, especially beyond 6 hours (see FIGS. 12A-12B). A single 30 mg phenserine slow release tablet was orally administered to three dogs over two days and drug activities monitored using acetylcholinesterase (ACHE) inhibition. Approximate steady-state levels of ACHE inhibition were achieved in each dog, however, substantial variability occurred between each of the dogs, again perhaps especially after 6 hours post dosing on each day. (see FIGS. 12A-12B). FIG. 12A illustrates individual variability whereas FIG. 12B illustrates the mean data provided in FIG. 12A.

Figure 13:
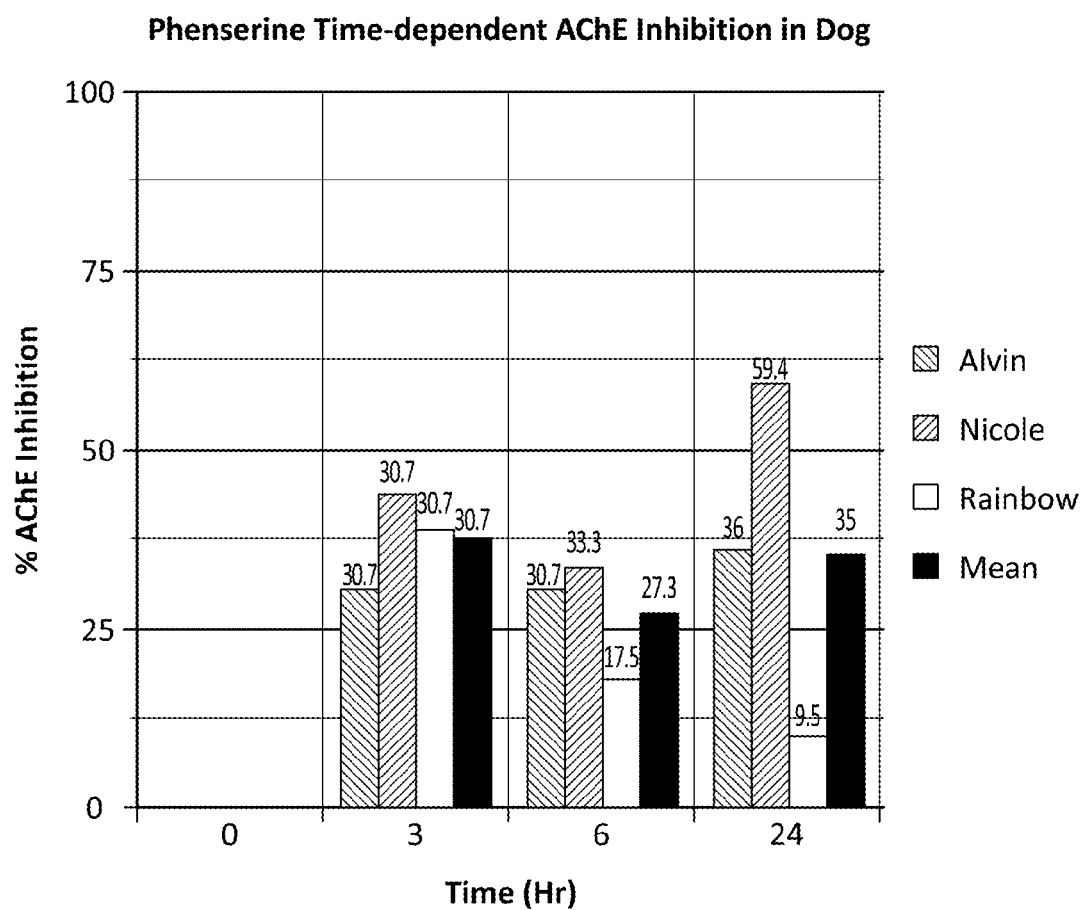
FIG. 13 illustrates in vivo acetylcholinesterase inhibition following administration of a slow release formulation containing phenserine.

In a second study, a single sustained release oral formulation of phenserine was administered to three separate dogs, which resulted in sustained acetylcholinesterase inhibition but also substantial variability among individuals (FIG. 13).

Figure 14A:
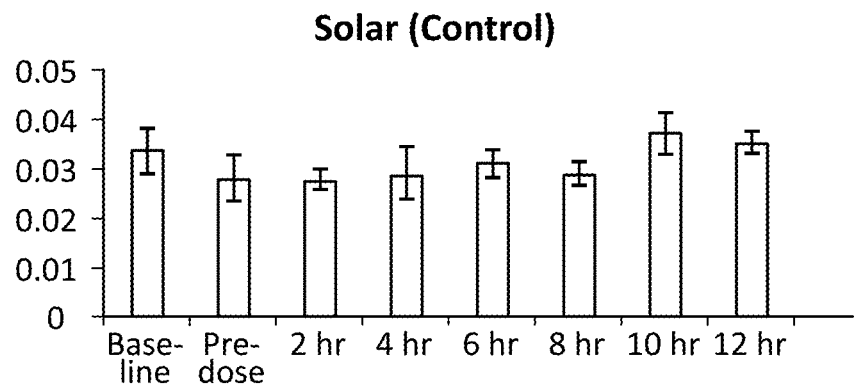
FIGS. 14A-14C illustrate in vivo acetylcholinesterase inhibition following a ten-day administration of a slow release formulation containing phenserine.
Figure 14B:
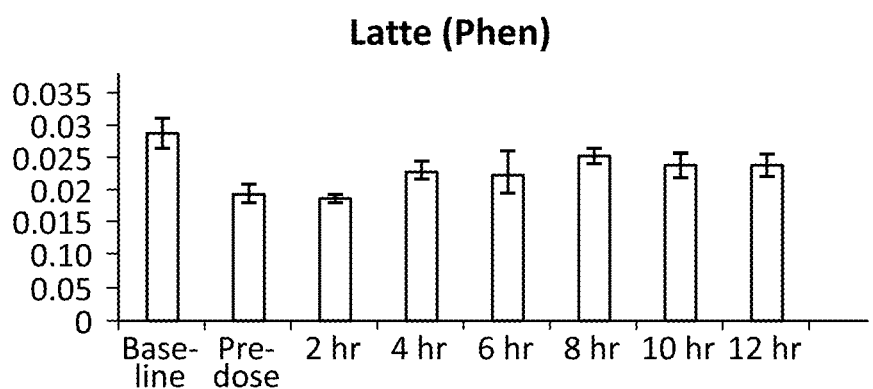
Figure 14C:
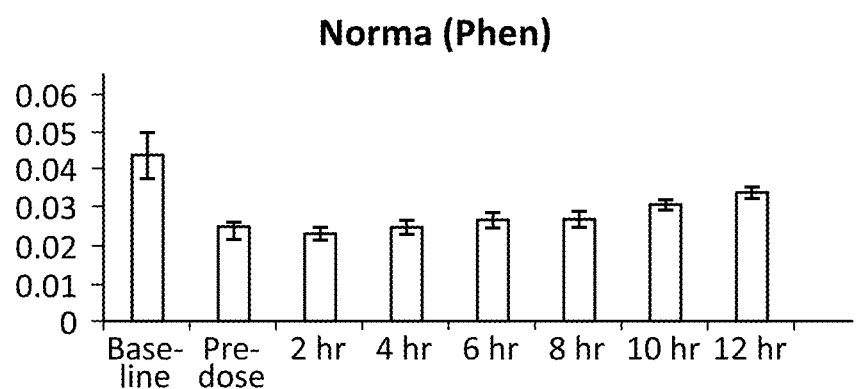

In a third study, the pharmacokinetics indicated by the pharmacodynamic effects of extended, controlled-release formulation of phenserine as an acetylcholinesterase inhibitor were determined. (FIGS. 14A-14C). Briefly, a 30 mg extended, controlled-release tablet of phenserine was administered daily for 10 days to two dogs (FIGS. 14B, 14C) and ACHE activities measured on day 10 in these two dogs and in one control (FIG. 14A) that received no drug for 10 days. Long term drug activity occurred in relation to the pre-trial baseline and control dog.

Example 8

Figure 15:
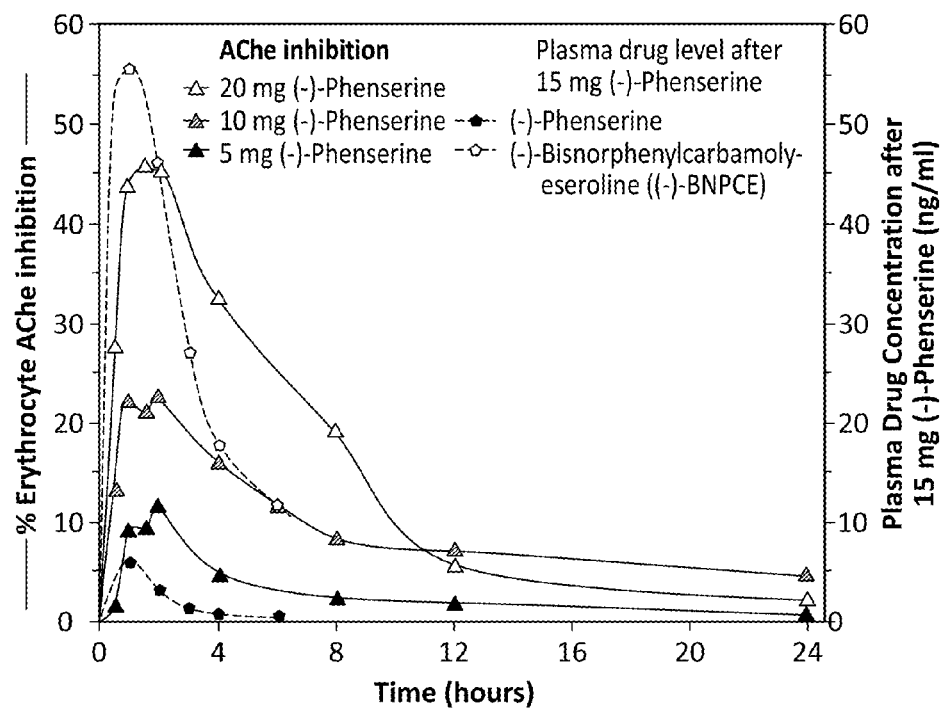
FIG. 15 illustrates time-dependent pharmacokinetics and pharmacodynamics following oral phenserine administration in vivo.

FIG. 15 shows the acetylcholinesterase inhibition in peripheral red blood cell membranes used as a marker to manage the effective concentration of phenserine and its metabolites, principally (−)-bisnorphenylcarbamoyleseroline (BNPCE), active in the brain. For example, to maintain a mean targeted $EC_{50}$ in the brain, within the range $EC_{40}$-50, phenserine would be dosed in a formulation that maintained in peripheral red blood cell membranes the effective concentration of phenserine and its metabolites.

The relationship between pharmacokinetic and pharmacodynamics evaluated in FIG. 15 was evaluated in aged volunteers. A total of 32 subjects (60-80 years of age, 11 males/21 females) were screened and enrolled. All participants provided informed consent, the conduct of the study were approved and overseen by the local Review IRB.

In brief, separate subjects were administered clinical grade phenserine tartrate orally at the doses of 5, 10 or 20 mg for pharmacodynamic ACHE evaluations. For pharmacokinetic (blood concentrations of primary drug and select metabolites) a dose of mg additionally was evaluated. Blood samples for pharmacokinetic/pharmacodynamics analyses were collected immediately prior to phenserine tartrate or placebo administration and at regular intervals for 24 hours afterwards. The initial eight subjects were randomly assigned to receive either 5 mg phenserine tartrate (six subjects) or placebo (two subjects), and in a similar manner dose escalation was made to 10 mg and 20 mg phenserine tartrate or placebo evaluation in separate groups of subjects (in a blinded manner). As described, a 15 mg phenserine tartrate dose was also evaluated for pharmacokinetics.

For pharmacokinetic analyses: Samples for plasma phenserine measurement were collected in 10 mL blood sample tubes containing ethylene diamine tetraacetic acid (EDTA) that were pre-chilled on wet ice. These were centrifuged within 15 min of collection, and stored in a freezer at −70° C. freezer in marked polypropylene tubes until analysis. Phenserine levels were quantified by liquid chromatography/mass spectrometry (LC/MS/MS). In brief, analyses were undertaken on Perkin-Elmer (PE, Norwalk, USA) high performance liquid chromatographic (HPLC) instrumentation. Compound separation was performed on a Phenomenex LUNA C18 column (5 μM, 2.0 mm×150 mm; Torrance, USA), with a Phenomenex guard column (2 mm×30 mm). The mobile phase was 60% acetonitrile (HPLC grade) plus 40% ammonium acetate (v/v) with a flow rate of 0.4 mL/min. (−)-N-methylphysostigmine prepared in 100% methanol was used as an internal standard, and had a retention time separate and shorter than phenserine. For extraction of phenserine from 0.5 mL plasma samples, a 25 μL sample internal standard was added combined with 10 mL of concentrated ammonium hydroxide. Thereafter, 2 mL of tert-butyl methyl ether was added and the sample was mixed and flash frozen. The organic layer was decanted, dried under a stream of nitrogen and reconstituted into 250 μL of mobile phase. Of this, a 60 μL sample was then injected into the HPLC.

Quantification of phenserine and internal standard was undertaken by MS (PE-Sciex API 365 triple-quadrupole MS), a PE-Sciex ionspray source and heated nebulizer (420 C), controlled by a Mac computer. Phenserine was detected by [M+H]+ ion of m/z 338 and a product ion of m/z 162, whereas the internal standard ((−)-N-methylphysostigmine) possessed a [M+H]+ ion of m/z 290 and a product ion of m/z 72. Detection was found to be linear over the concentration range of 0.25-250 ng/mL, with a mean relative standard deviation (SD) of 5.7%.

For pharmacodynamics ACHE inhibition analyses: erythrocyte ACHE levels were evaluated in whole blood samples by using methods known in the art. Briefly, duplicate samples of freshly collected whole blood were analyzed. Cholinesterase activity, U/L, was detected at 37° C. using a differential pH procedure on a Eurochem CL-10 (Rome, Italy). The time-course of enzyme inhibition was determined for each subject by expressing each mean post-phenserine administration ACHE concentration as a fraction of the mean pre-administration resting level of ACHE within the same individual. This value was then subtracted from 1 and multiplied by 100% to provide percent ACHE inhibition.

Table 1, below, discloses a comparison of the plasma concentrations of phenserine and its metabolites in human, beagle dog, and wistar rat plasma.

Table 1

A comparison of the plasma concentrations of phenserine and its metabolites in human, beagle dog, and wistar rat plasma.

| | | Average Plasma Concentrations (ng/mL) | | | | | |
|---|---|---|---|---|---|---|---|
| Hour | Species | phen-serine | N8-nor-phen-sereine | N1-nor-phen-sereine | N1,N8-bisnor-phen-sereine | 4-OH-phen-serine | rub-reserine |
| 1 | Human | 3.02 | 11.2 | 1.56 | 22.5 | 0.033 | 5.60 |
| | Dog | 4.95 | 33.4 | 86.1 | 235 | 6.02 | 6.30 |
| | Rat | N/A | 96.4 | 37.6 | 536 | 1.41 | 2.00 |

Table 1-continued

A comparison of the plasma concentrations of phenserine and its metabolites in human, beagle dog, and wistar rat plasma.

| | | Average Plasma Concentrations (ng/mL) | | | | | |
|---|---|---|---|---|---|---|---|
| Hour | Species | phenserine | N8-nor-phensereine | N1-nor-phensereine | N1,N8-bisnor-phensereine | 4-OH-phenserine | rubreserine |
| 2 | Human | 2.09 | 7.38 | 1.19 | 14.5 | 0.024 | 6.82 |
|   | Dog | 15.4 | 28.2 | 50.3 | 220 | 8.54 | 9.18 |
|   | Rat | N/A | 69.2 | 26.2 | 539 | 0.97 | 2.61 |
| 3 | Human | 1.08 | 4.28 | 0.80 | 7.62 | *BQL | 5.26 |
|   | Dog | 0.71 | 9.06 | 86.7 | 428 | 1.11 | 3.69 |
| 4 | Human | 0.31 | 3.61 | 0.53 | 6.55 | *BQL | 1.88 |
|   | Dog | 0.97 | 7.88 | 41.9 | 351 | 1.10 | 4.04 |

*BQL = below quantifiable limit

Example 9

Figure 16:
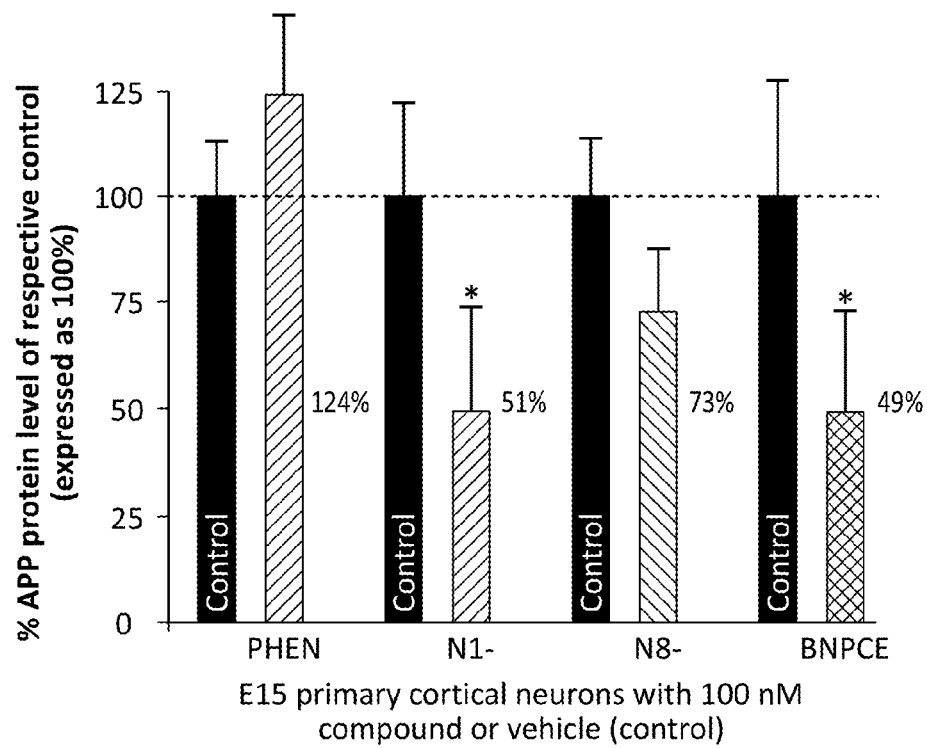
FIG. 16 illustrates inhibition of amyloid precursor protein in the presence of phenserine.

In FIG. 16 inhibition of amyloid precursor protein is used as an example of the in vivo activity levels of phenserine and its metabolites in the brain.

Primary cortical neurons were harvested and isolated from mice, and then were cultured in line with methodologies known in the art. In brief, embryonic day 15-18 mouse pups were obtained from timed pregnant female mice (5 pups). Within a laminar flow cell culture hood, the brain was removed from these mouse pups and the meninges and blood vessels were carefully removed. The cerebral cortex was dissected out and placed in chilled Eppendorf tubes containing 500 µL of Hank's Balanced Salt Solution (HBSS), without $Ca^{+2}/Mg^{+2}$ salts, that was supplemented with 1 mM sodium pyruvate and 10 mM HEPES, and possessed a pH of 7.4. Maintained on wet ice, individual cells were then isolated by titrating some 10 times to dissociate cells by use of using a glass pasture pipette with a fire polished tip. Cell culture medium was increased to a volume of 1.5 mL, by addition of 1 mL of HBSS that contained $Ca^{+2}/Mg^{+2}$ salts together with Na pyruvate+HEPES, to thereby restore divalent cations. The supernatant was carefully removed, placed into 15 mL tubes and centrifuged (60 sec, 900 rpm, 4° C.). The pellet was resuspended into 2 mL of HBSS containing $Ca^{+2}/Mg^{+2}$ salts+Na pyruvate+HEPES and an aliquot removed for cell evaluation and counting. Thereafter, approximately $1 \times 10^5$ cells/well were plated into 24-well plates, or $2 \times 10^5$ in 12-well plates. These plates were pre-coated with poly D-lysine containing poly L-lysine coverslips to allow immunocytochemical confirmation of neuronal integrity.

Following maintenance in cell culture (>24 h) primary cortical neurons were challenged to known concentrations of experimental drugs for 48 h, or vehicle (culture media) alone. Cytoplasmic protein lysates were generated by homogenizing the cells in midRIPA buffer (25 mM Tris pH 7.4, 1% NP40, 0.5% sodium deoxycholate, 15 mM NaCl, protease inhibitors, RNase inhibitor, and 10 µM DTT). Quantification of select proteins, for example AAP was undertaken by Western Blotting using the APP N-terminal antibody (22C11) obtained from Chemicon (Temecula, Calif.). The housekeeping protein β-actin quantified in the same samples to allow normalization, and was probed with anti-β-actin (Chemicon). The Western blots were developed by using chemiluminescence (PIERCE), were visualized with a PhosphoImager (BioRad, Hercules, Calif.), and resulting bands were quantified by QuantityOne software (BioRad).

Example 10

Figure 17:
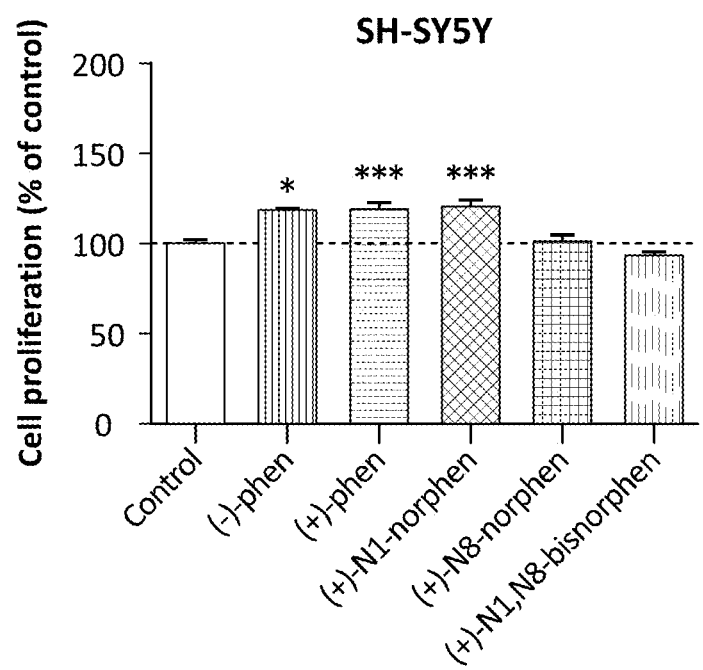
FIG. 17 illustrates effects of phenserine on cell proliferation in vitro.

Phenserine affects neurogenesis (FIG. 17). Briefly, (+)- and (−)-phenserine induce neurotrophic actions, as assessed by increasing cellular proliferation of SH-SY5Y cells. SHSY5Y cells were exposed for 24 h to 30 mM concentration of (−)- and (+)-phenserine. After 24 h cell proliferation was determined by MTS assay. *P,0.05, p,0.01, and *p,0.001 compared to control samples without drug.

The disclosed compounds are able to positively impact neurogenesis on multiple levels. First, phenserine and analogues have been demonstrated to enhance neural precursor cell viability in cell culture—increasing neurosphere size and augmenting their survival. Second, in cellular and animal studies high levels of APP (which are elevated by TBI) induce the differentiation of neural precursor cells towards a glial phenotype, and away from a neuronal one. This action is reversed by phenserine and analogues. Third, Phenserine and analogues elevate neurotrophic factor levels in brain—as assessed by measuring BDNF, a key regulator of neurogenesis. In both wild type and AD transgenic mice, administration of phenserine analogues augmented neurogenesis.

Example 11

For each of the forthcoming illustrative treatment scenarios provided in Examples 11-14, the extended, controlled-release composition could be combined with an anti-inflammatory drug.

A patient presents with a witness who states that about an hour ago this 20-year-old male hit his head after falling during a soccer practice. He was momentarily unconscious and dazed as he attempted to stand. The patient currently complains of a headache. After history and physical examination, the physician diagnoses a concussion using the current criteria. To establish a baseline of current status the physician carefully records his findings, the Glasgow Coma Scale score, the observations made by the medical ambulance staff and orders the patient to rest in bed until the headache subsides and to avoid mental effort until the headache subsides. The physician orders a blood sample to measure C-Reactive Protein. The physician orders an extended, controlled-release tablet of phenserine prescribed to release 3.5 mg/h phenserine for 8 hours and is prescribed to be taken by mouth immediately and then at 8 hour intervals daily. The physician plans to see the patient weekly to reassess his status using each of the baseline evaluations. Over one month the patient steadily improves and then stabilizes on the measures being assessed. Using the above dosing guidelines, the physician discontinues the drug treatment or course and, on reassessments over the next month, there is no deterioration and C-Reactive Protein levels recover into the normal range. The patient is discharged and warned not to risk further head injuries.

Example 12

A 25-year-old female presents stating that about four hours ago she fell badly at home and hit her head on the floor. There is a bruise developing on the left forehead. She gives the history that she had a concussion two months earlier that may have left her easily becoming dizzy and feeling not as mentally alert as she felt prior to the injury. Upon further questioning and examination there is no evidence to support a diagnosis of traumatic brain injury or concussion. In view of her history of recent concussion and a current head injury she is considered to be at risk from sub-concussive injury and treatment with phenserine using a daily oral formulation of an extended, controlled-release gel capsule that provides 1 mg/h of phenserine over 24 hours is begun immediately with instructions to take one pill daily upon arising. She is evaluated using the Mini Mental State Examination and asked to return weekly. Upon reexamination no changes in her condition are found and at one-month studies of inflammatory markers in plasma prove within normal limits. She is discontinued from dosing and reevaluated including plasma inflammatory markers at six weeks and, with increases in values of the latter she is restarted on drug for one additional month. After discontinuing drug, repeated testing finds that plasma inflammatory markers have returned within normal limits and she is discharged from treatment.

Example 13

A 75-year-old male is brought in by his wife with the concern that he had fallen badly at home. It is not known whether he hit his head during the fall. After history and physical examination, he exhibits no criteria to diagnoses either traumatic brain injury or concussion. The risks of possible sub-concussive injury are discussed with the family and they express concerns, shared by the patient, that due to his age he may be vulnerable to some deterioration in brain function due to a sub-concussive injury. The doctor evaluates that there are no special conditions indicating against treatment and agrees with the family to start dosing with phenserine in an extended, controlled-release pill prescribed to deliver 2 mg/h phenserine for 24 hours with instructions to take one pill every morning upon rising. The patient is seen regularly and evaluated clinically and by reports from the spouse each of which remain unremarkable. The doctor decides to extend dosing for two months and then follow the patient at three months to evaluate his course. No changes at three months allow the doctor to terminate care.

Example 14

A 36-year-old male professional football player presents with a concern that he may be at risk during the upcoming practice and playing season from concussions. He reports at least one concussion prior to his professional career while in college play and a second at age 28. Both resolved without obvious impairments. He states he is at risk of further concussions and sub-concussive injuries and requests whatever prevention or protection is possible. The doctor prescribes a single immediate release 10 mg phenserine tablet to be taken immediately followed by a daily dosing oral formulation (an extended, controlled-release pill prescribed to release 5 mg/h for 12 h) with instructions to take one pill every morning upon arising and every evening with a meal until the playing and practice seasons have ended. To ensure that an adequate brain concentration of drug is present the doctor orders an immediate, followed by one week after starting dosing, acetylcholinesterase activity assay of blood samples. The second assay reveals 51 percent of the earlier pretreatment activity, a value associated with the IC50 for N1, N8-bisnorphenylcarbamoyleseroline or a brain concentration of 100 nM. Since this is within the active range of the drug the doctor advises the patient to continue the current dosing.

Abbreviated List of Defined Terms

To assist in understanding the scope and content of the foregoing written description and appended claims, a select few terms are defined directly below. Unless defined otherwise, all technical and scientific terms used herein have the same meaning as commonly understood by one of ordinary skill in the art to which the present disclosure pertains.

The term "anecrotic cell death" and similar terms, as used herein, refers to cell death occurring through means other than those caused by external factors such as trauma or infection. As used herein, "anecrotic cell death" is understood to include premature, controlled, and/or self-initiated/programmed cell death pathways that result in the death of a cell, such as apoptosis and/or autophagy and may, when appropriate, be understood to include alternative programmed cell death pathways such as necroptosis.

As used herein, the term "anti-inflammatory drug" refers to those medicaments that resolve, antagonize, ameliorate, or prevent the inflammatory response and/or symptoms related thereto. This term, as used herein, specifically includes steroids and non-steroidal anti-inflammatory drugs, as defined herein. Additionally, the term "anti-inflammatory drug" is intended to include acetylsalicylic acid, commonly referred to as aspirin. Additionally, and even though it has demonstrated little to no anti-inflammatory effects as a medicament, acetaminophen is specifically meant to be included within the scope of the term "anti-inflammatory drug."

As used herein, the term "brain trauma" refers to a physical injury of or to the brain or related tissue and encompasses a wide range of trauma, including sub-concussive injury, concussion (mTBI), TBI, persistent post-concussion syndrome, and chronic traumatic encephalopathy. The term "brain trauma" is intended to additionally encompass the induction of neuronal dysfunction and or anecrotic cell death as manifested by clinical losses of functions regarded as associated with the affected neurons and occurring in the presence of traumatic brain injury of various degrees including concussion and sub-concussion or neurodegenerative diseases, each of which is associated with pathologies that are regarded as providing environments unfavorable to the survival of neurons physiological effects or sequelae subsequent a physical injury to the brain. For example, the term "brain trauma," as used herein includes a physical injury to the brain (e.g., caused by a concussive impact to the head) as well as the negative effects of the resulting hostile environment within the affected neural tissue that promotes anecrotic cell death of neurons. Additionally and/or cumulatively, the term "brain trauma" is intended to broadly encompass the cascade of pathologies that follow physical injury to the brain (e.g., TBI, mTBI, sub-concussive injury, etc.), neurodegenerative disorders, and/or other types of brain traumas, as defined herein. Said cascade of pathologies include, but are not limited to, inflammation, oxidative stress, beta-amyloid stress, glutamate induced excitotoxicity, and/or any neuropathological degenerative, clinical cognitive, and/or other impairments of the brain resulting from brain trauma, as defined herein. Additionally, the term "brain trauma" is intended to encompass neurodegeneration, generally, and is also intended to encompass neurodegenerative disorders such as Parkinson's disease, Alzheimer's disease, and so forth.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," "involves," "contains," etc.), and similar terms as used herein, including within the claims, shall be inclusive and/or open-ended, shall have the same meaning as the word "comprising" and variants thereof (e.g., "comprise" and "comprises"), and do not exclude additional un-recited elements or method steps, illustratively.

Various aspects of the present disclosure, including compositions, devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure includes a specific reference to one or more embodiments thereof, and vice versa, and is intended to provide illustrative examples without limiting the scope of the disclosure, which is indicated by the appended claims rather than by the following description.

As used herein, the term "medicament" refers to any substance used for medical treatment and particularly refers to the various forms in which substances for medical treatment may be provided. For example, medicaments include substances used for medical treatment provided in the form of a tablet, capsule, liquid suspension, injectable, transdermal formulation (e.g., a patch that delivers the active ingredient transdermally), lozenge, gel, nanoparticle, microparticle, polymer formulations, or other form(s) known in the art of drug delivery.

As used herein, the term "non-steroidal anti-inflammatory drug," which may also be referred to herein by the acronym "NSAID," includes the class of substances (and medicaments including said class of substances) that when consumed, absorbed, inhaled, injected, smoked, or otherwise received into the body provide analgesic, antipyretic, and/or anti-inflammatory effects. NSAIDs include acetylsalicylic acid (aspirin), ibuprofen, ketoprofen, naproxen, meloxicam, piroxicam, celecoxib, and any other NSAID, including any pharmaceutically acceptable salts thereof, as known in the art.

As used herein, the term "phenserine" includes the organic compound (−)-phenserine of Formula 1:

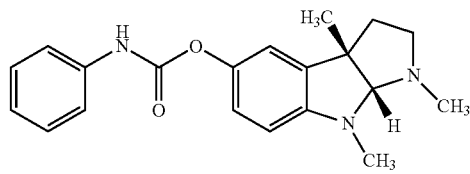

Formula 1

The term "phenserine" is broadly understood to encompass both enantiomers of phenserine, individually and as a racemic mixture; however, unless otherwise specifically indicated, the term "phenserine" as used herein refers to the (−)-phenserine enantiomer of Formula 1. The term "phenserine," as used herein also encompass phenserine metabolites, phenserine prodrugs, or combinations thereof. The term "phenserine metabolite" includes metabolic derivatives of phenserine, particularly any of: (−)-N1, N8-bisnorphenylcarbamoyleseroline of Formula 2;

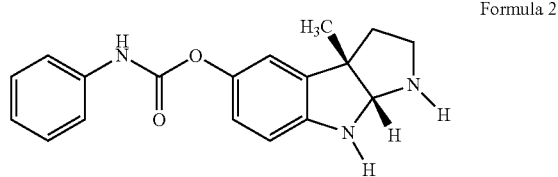 [SMILES: C[C@@]12CCN[C@@H]1Nc1ccc(OC(=O)Nc3ccccc3)cc12]

Formula 2

(−)-N1-norphenylcarbamoyleseroline of Formula 3; and/or

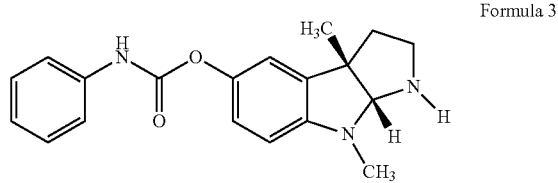 [SMILES: CN1c2ccc(OC(=O)Nc3ccccc3)cc2[C@]2(C)CCN[C@H]12]

Formula 3

(−)-N8-norphenylcarbamoyleseroline of Formula 4.

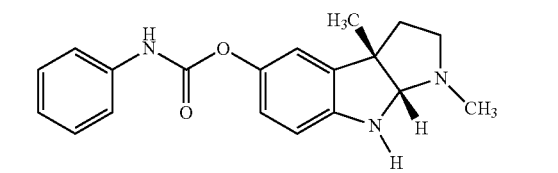

Formula 4

Additionally, the terms "phenserine," "phenserine metabolite," or similar are understood to include any pharmaceutically acceptable salts thereof.

The term "steroid," as used herein, includes the class of anti-inflammatory organic compounds known in the art as corticosteroids (e.g., betamethasone, dexamethasone, cortisone, hydrocortisone, methylprednisolone, prednisolone, fludrocortisone, etc.) and is exclusive of the class of anabolic steroids. As used herein, steroids may be administered orally, intravenously, and/or intramuscularly.

The term "therapeutically acceptable daily dose," as used herein, refers to dosages of disclosed compounds that are approved by the Food and Drug Administration for human use and is within the purview of one having ordinary skill in the art. For some compounds, the therapeutically acceptable daily dose is known to vary depending on a variety of factors, including age, gender, pregnancy, or other factors. Additionally, the term "therapeutically acceptable daily dose" includes therapeutic dosages of a compound up to the maximum daily dose of said compound and any lesser dosage that provides a therapeutic benefit. As a non-limiting example, the therapeutically acceptable daily dose of acetaminophen is no more than 4,000 mg and is commonly provided in 325 mg or 500 mg tablets. Accordingly, a therapeutically acceptable daily dose of acetaminophen includes a single daily dose of as little as 325 mg to multiple doses that are cumulatively less than 4,000 mg in a 24-hour period. As an additional, non-limiting example, a "therapeutically acceptable daily dose" of oral formulations of dexamethasone comprise 0.75 mg to 9 mg per day in divided doses every 6 to 12 hours. As an additional, non-limiting example, a "therapeutically acceptable daily dose" of acetylsalicylic acid (aspirin) includes the adult low-dose aspirin dose of 81 mg/day up to an adult regular strength dose of 325 mg, which may be taken up to a total of 3900 mg/day. In some cases, 75 mg/day of aspirin have been shown to be effective; thus, where appropriate, any of the foregoing dosages of aspirin are included within the meaning of a "therapeutically acceptable daily dose."

CONCLUSION

Modifications to brain trauma pathologies by compositions and treatment methods disclosed herein can preserve brain functions and provide beneficial effects such as preventing clinical sequelae from traumatic brain injury, concussion, and sub-concussive injury. The combinations of in vitro and in vivo results disclosed herein meet the standard that successful invention depends upon to soundly model and predict utility in the presence of human disease such as traumatic brain injury, concussion, and sub-concussive injury (or other brain traumas).

Any headings used herein are for organizational purposes only and are not meant to be used to limit the scope of the description or the claims.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative compositions, methods, apparatus, and the like are not described herein in particular detail in order to avoid obscuring aspects of the example embodiments. Such aspects are, however, also contemplated herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

The present disclosure may be embodied in other specific forms without departing from its spirit or essential characteristics. The described embodiments are to be considered in all respects only as illustrative and not restrictive. The scope of the disclosure and any claimed invention derived therefrom is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the compositions, methods, products, devices, and apparatus disclosed herein may be made without departing from the scope of the disclosure, which is defined in the appended claims. All changes which come within the meaning and range of equivalency of the claims are to be embraced within their scope.

What is claimed is:

1. A method for treating concussion, the method comprising:
   administering a therapeutic dose of an active compound comprising one or more of: phenserine, a phenserine metabolite, a phenserine prodrug, or combinations thereof.

2. The method as in claim 1, further comprising maintaining the therapeutic dose of the active compound at therapeutically effective concentrations over a treatment period.

3. The method as in claim 2, wherein the therapeutic dose of the active compound is administered as an extended, controlled-release medicament.

4. The method as in claim 3, wherein the extended, controlled-release medicament comprises between about 5-150 mg of the active compound, and wherein maintaining the therapeutic dose of the active compound comprises administering the extended, controlled-release medicament between about 8-24 hours over the treatment period.

5. The method as in claim 4, wherein the treatment period is at least one week.

6. The method as in claim 3, wherein the extended, controlled-release medicament comprises between about 15-60 mg of the active compound, and wherein maintaining the therapeutic dose of the active compound comprises administering the extended, controlled-release medicament wherein the extended, controlled-release medicament is administered orally or sublingually at least about every 24 hours.

7. The method as in claim 2, wherein the treatment period comprises a duration in which one or more of inflammatory markers are elevated from a steady-state level or one or more diagnostic criteria indicate an ongoing concussion or a continued risk of concussion.

8. The method as in claim 2, wherein maintaining the therapeutic dose of the active compound comprises:
   obtaining a blood sample comprising peripheral red blood cells;
   assaying an acetylcholinesterase activity in the peripheral red blood cells; and adjusting the extended, controlled-release therapeutic dose of the active compound to provide the therapeutically effective concentration of the active compound.

9. The method as in claim 8, wherein the therapeutically effective concentration of the active compound is greater than about 1 nM in peripheral blood.

10. The method as in claim 9, wherein the therapeutically effective concentration of the active compound is between about 25-100 nM in peripheral blood.

11. The method as in claim 1, further comprising:
administering a therapeutically acceptable daily dose of a second active compound, wherein the second active compound comprises an anti-inflammatory drug; and
maintaining the therapeutically acceptable daily dose of the second active compound at therapeutically effective concentrations over the period of time, wherein the second active compound acts additively or synergistically with the first active compound.

12. The method as in claim 11, wherein the anti-inflammatory drug comprises acetylsalicylic acid.

13. The method as in claim 11, wherein the anti-inflammatory drug comprises acetaminophen.

14. The method as in claim 11, wherein the anti-inflammatory drug comprises a corticosteroid.

15. The method as in claim 11, wherein the anti-inflammatory drug comprises a non-steroidal anti-inflammatory drug.

16. A method for preventing an onset of anecrotic cell death in neurons or mitigating one or more pathologies following brain trauma, the method comprising:
administering an extended, controlled-release therapeutic dose of an active compound, wherein the active compound comprises one or more of: phenserine, a phenserine metabolite, a phenserine prodrug, or combinations thereof; and
maintaining the extended, controlled-release therapeutic dose of the active compound at therapeutically effective concentrations over a period of time.

17. The method as in claim 16, wherein the extended, controlled-release therapeutic dose of the active compound is administered to an individual after a predicted onset of anecrotic cell death in neurons or after presentation of the one or more pathologies following brain trauma.

18. The method as in claim 16, wherein the extended, controlled-release therapeutic dose of the active compound is administered to an individual at risk of a predicted onset of anecrotic cell death in neurons or at risk of the one or more pathologies following brain trauma.

19. The method as in claim 16, the method further comprising:
obtaining a blood sample comprising peripheral red blood cells;
assaying an acetylcholinesterase activity in the peripheral red blood cells; and
adjusting the extended, controlled-release therapeutic dose of the active compound to provide a prescribed concentration of the active compound.

20. The method as in claim 19, wherein the prescribed concentration of the active compound is in a range of about 1-250 nM as measured in the peripheral blood.

21. The method as in claim 19, further comprising:
administering a therapeutically acceptable daily dose of a second active compound, wherein the second active compound comprises an anti-inflammatory drug; and
maintaining the therapeutically acceptable daily dose of the second active compound at therapeutically effective concentrations over the period of time, wherein the second active compound acts additively or synergistically with the first active compound.

22. The method as in claim 21, wherein administering the extended, controlled-release therapeutic dose of the active compound and the therapeutically acceptable daily dose of the second active compound comprises:
administering said compounds orally in a form selected from the group consisting of: a tablet, a capsule, a pill, a liquid, and a gel; or
administering said compounds in a manner selected from the group consisting of: sublingually, intravenously, subcutaneously, transdermally, nasally, and intramuscularly.

* * * * *